(12) United States Patent
Kasahara et al.

(10) Patent No.: US 8,105,231 B2
(45) Date of Patent: Jan. 31, 2012

(54) LIVING-BODY TISSUE REMOVING APPARATUS

(75) Inventors: Hideyuki Kasahara, Tokyo (JP); Takahiro Kogasaka, Tokyo (JP)

(73) Assignees: Olympus Corporation, Tokyo (JP); Terumo Kabushiki Kaisha, Tokyo (JP)

( * ) Notice: Subject to any disclaimer, the term of this patent is extended or adjusted under 35 U.S.C. 154(b) by 395 days.

(21) Appl. No.: 10/976,213

(22) Filed: Oct. 27, 2004

(65) Prior Publication Data

US 2005/0154257 A1 Jul. 14, 2005

Related U.S. Application Data

(60) Provisional application No. 60/516,649, filed on Oct. 31, 2003.

(51) Int. Cl.
*A61B 1/00* (2006.01)
*A61B 17/22* (2006.01)
*A61D 1/02* (2006.01)

(52) U.S. Cl. .................. 600/114; 600/104; 606/159

(58) Field of Classification Search .......... 600/104, 600/114, 127, 129, 153, 156, 175, 176, 158, 600/157, 146, 105, 106; 604/23, 164.11, 604/164.01, 164.09, 164.93, 48, 93.01, 96.01; 606/159

See application file for complete search history.

(56) References Cited

U.S. PATENT DOCUMENTS

| 3,145,249 A | | 8/1964 | Meltzer | |
|---|---|---|---|---|
| 4,083,585 A | | 4/1978 | Helm | |
| 4,793,346 A | * | 12/1988 | Mindich | 606/28 |
| 5,013,312 A | | 5/1991 | Parins et al. | |
| 5,088,998 A | | 2/1992 | Sakashita et al. | |
| 5,129,885 A | | 7/1992 | Green et al. | |
| 5,320,091 A | * | 6/1994 | Grossi et al. | 600/104 |
| 5,349,940 A | | 9/1994 | Takahashi et al. | |
| 5,350,393 A | | 9/1994 | Yoon | |
| 5,373,840 A | * | 12/1994 | Knighton | 600/106 |
| 5,386,817 A | * | 2/1995 | Jones | 600/104 |
| 5,403,312 A | * | 4/1995 | Yates et al. | 606/50 |
| 5,509,892 A | * | 4/1996 | Bonnet | 600/156 |
| 5,518,502 A | | 5/1996 | Kaplan et al. | |
| 5,575,756 A | * | 11/1996 | Karasawa et al. | 600/157 |
| 5,695,448 A | * | 12/1997 | Kimura et al. | 600/121 |
| 5,697,946 A | | 12/1997 | Hopper et al. | |
| 5,738,628 A | * | 4/1998 | Sierocuk et al. | 600/104 |

(Continued)

FOREIGN PATENT DOCUMENTS

DE 39 17 465 C2 4/1992

(Continued)

OTHER PUBLICATIONS

Definition of coronoid Retrieved on Oct. 30, 2007 from Online Medical Dictionary http://cancerweb.ncl.ac.uk/cgi-bin/omd?coronoid.*

(Continued)

*Primary Examiner* — Anhtuan Nguyen
*Assistant Examiner* — Alireza Nia
(74) *Attorney, Agent, or Firm* — Holtz, Holtz, Goodman & Chick, PC

(57) ABSTRACT

A living-body tissue removing apparatus includes a grip portion, an inserting portion which is connected to the grip portion and is inserted in the body, and an air feed channel which feeds predetermined air in the inserting portion so as to discharge the predetermined air from an opening arranged to the inserting portion.

11 Claims, 26 Drawing Sheets

U.S. PATENT DOCUMENTS

| | | | | |
|---|---|---|---|---|
| 5,759,150 | A * | 6/1998 | Konou et al. | 600/114 |
| 5,807,402 | A | 9/1998 | Yoon | |
| RE36,043 | E | 1/1999 | Knighton | |
| 5,891,141 | A * | 4/1999 | Rydell | 606/45 |
| 5,895,353 | A * | 4/1999 | Lunsford et al. | 600/209 |
| 5,902,315 | A * | 5/1999 | DuBois | 606/190 |
| 5,908,429 | A * | 6/1999 | Yoon | 606/144 |
| 5,913,866 | A | 6/1999 | Ginn et al. | |
| 5,913,870 | A | 6/1999 | DeFonzo et al. | |
| 5,916,233 | A * | 6/1999 | Chin | 606/190 |
| 5,928,135 | A * | 7/1999 | Knight et al. | 600/104 |
| 5,938,680 | A * | 8/1999 | Ginn | 606/190 |
| 5,993,384 | A | 11/1999 | Lunsford et al. | |
| 6,019,720 | A | 2/2000 | Bito | |
| 6,019,771 | A | 2/2000 | Bennett | |
| 6,080,102 | A | 6/2000 | Konou et al. | |
| 6,162,173 | A | 12/2000 | Chin et al. | |
| 6,176,825 | B1 * | 1/2001 | Chin et al. | 600/205 |
| 6,193,653 | B1 * | 2/2001 | Evans et al. | 600/210 |
| 6,206,823 | B1 * | 3/2001 | Kolata et al. | 600/129 |
| 6,352,531 | B1 | 3/2002 | O'Connor et al. | |
| 6,406,425 | B1 | 6/2002 | Chin et al. | |
| 6,471,638 | B1 | 10/2002 | Chang et al. | |
| 6,523,231 | B1 | 2/2003 | Lassiter | |
| 6,527,771 | B1 * | 3/2003 | Weadock et al. | 606/50 |
| 6,755,782 | B2 | 6/2004 | Ogawa | |
| 6,804,866 | B2 | 10/2004 | Lemke et al. | |
| 6,830,546 | B1 | 12/2004 | Chin et al. | |
| 6,860,516 | B2 * | 3/2005 | Ouchi et al. | 285/124.1 |
| 6,863,661 | B2 | 3/2005 | Carrillo, Jr. et al. | |
| 6,863,674 | B2 | 3/2005 | Kasahara et al. | |
| 6,923,759 | B2 | 8/2005 | Kasahara et al. | |
| 7,077,803 | B2 | 7/2006 | Kasahara et al. | |
| 7,316,683 | B2 | 1/2008 | Kasahara et al. | |
| 7,645,289 | B2 * | 1/2010 | Bayer | 606/159 |
| 2003/0065349 | A1 * | 4/2003 | Hess et al. | 606/159 |
| 2003/0130674 | A1 | 7/2003 | Kasahara et al. | |
| 2003/0130675 | A1 | 7/2003 | Kasahara et al. | |
| 2004/0204725 | A1 | 10/2004 | Bayer | |
| 2005/0148817 | A1 | 7/2005 | Kasahara et al. | |
| 2005/0149094 | A1 | 7/2005 | Kasahara et al. | |
| 2005/0154257 | A1 | 7/2005 | Kasahara et al. | |
| 2005/0159764 | A1 | 7/2005 | Kasahara et al. | |
| 2006/0074444 | A1 | 4/2006 | Lin et al. | |
| 2007/0149993 | A1 | 6/2007 | Kasahara et al. | |

FOREIGN PATENT DOCUMENTS

| | | |
|---|---|---|
| EP | 0 479 565 A2 * | 4/1992 |
| EP | 0 761 171 A2 | 3/1997 |
| EP | 1 323 381 A1 | 7/2003 |
| JP | 58-61723 A | 4/1983 |
| JP | 1-204637 A | 8/1989 |
| JP | 03-162845 A | 7/1991 |
| JP | 4-221539 A | 8/1992 |
| JP | 4-362912 A | 12/1992 |
| JP | 08-029699 A | 2/1996 |
| JP | 9-075354 A | 3/1997 |
| JP | 09-140721 A | 6/1997 |
| JP | 10-071119 A | 3/1998 |
| JP | 2000-037347 A | 2/2000 |
| JP | 2000-37389 A | 2/2000 |
| JP | 2003-190171 A | 7/2003 |
| JP | 2003-199747 A | 7/2003 |
| JP | 2003-199754 A | 7/2003 |
| JP | 2003-199765 A | 7/2003 |
| JP | 2003-199766 A | 7/2003 |
| JP | 2003-305051 A | 10/2003 |
| JP | 2003-310628 A | 11/2003 |
| JP | 2004-008241 A | 1/2004 |
| JP | 2004-0652679 A | 3/2004 |
| WO | WO 97/26831 A1 | 7/1997 |
| WO | WO 00/40160 A2 | 7/2000 |

OTHER PUBLICATIONS

Related U.S. Appl. No. 10/976,212, filed Oct. 27, 2004, Inventor H. Kasahara.
Related U.S. Appl. No. 10/976,228, filed Oct. 27, 2004, Inventor H. Kasahara.
Related U.S. Appl. No. 10/976,229, filed Oct. 27, 2004, Inventor H. Kasahara.
Guidant, "A Guide to Vasoview® Uniport Plus EVH System," 2003.
510(k) Summary for VasoView® 6 Harvesting Cannula, 510(k) No. K022718, Aug. 28, 2002.
Japanese Office Action dated Oct. 31, 2006 (and English translation thereof) issued in JP Appln. No. 2001-401938, which is a counterpart application of related U.S. Appl. No. 11/564,763 (published as U.S. Publication No. 2007/0149993).
Japanese Office Action dated Jun. 13, 2006 (and English translation thereof) issued in JP Appln. No. 2001-401938, which is a counterpart application of related U.S. Appl. No. 10/329,822 (published as U.S. Publication No. 2003/0130674).
European Office Action dated May 11, 2006 issued in EP 02 028 642-3-2318, which is a counterpart application of related U.S. Appl. No. 10/329,822 (published as U.S. Publication No. 2003/0130674).
European Office Action dated Mar. 30, 2007 issued in EP 02 028 642-3-2318, which is a counterpart application of related U.S. Appl. No. 10/329,822 (published as U.S. Publication No. 2003/0130674).
European Search Report dated Apr. 14, 2003 issued in EP 02 028 642-3-2318, which is a counterpart application of related U.S. Appl. No. 10/329,822 (published as U.S. Publication No. 2003/0130674).
Notice of Allowance dated Aug. 25, 2008 issued in a counterpart application of related U.S. Appl. No. 10/329,822 (published as U.S. Publication No. 2003/0130674).
Japanese Office Action dated Apr. 27, 2010 issued in counterpart Japanese Application No. 2006-544698.

* cited by examiner

29a

29a

29a

29a

29a

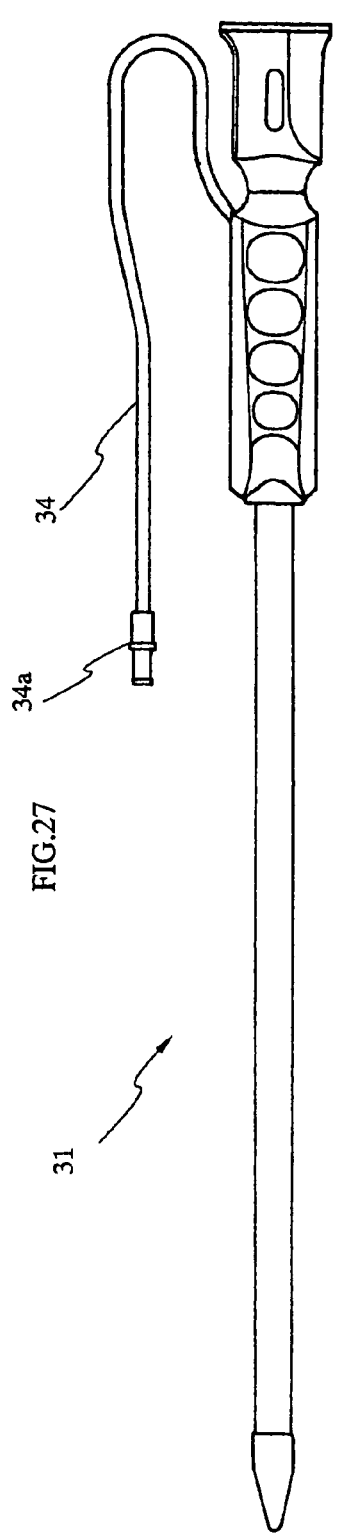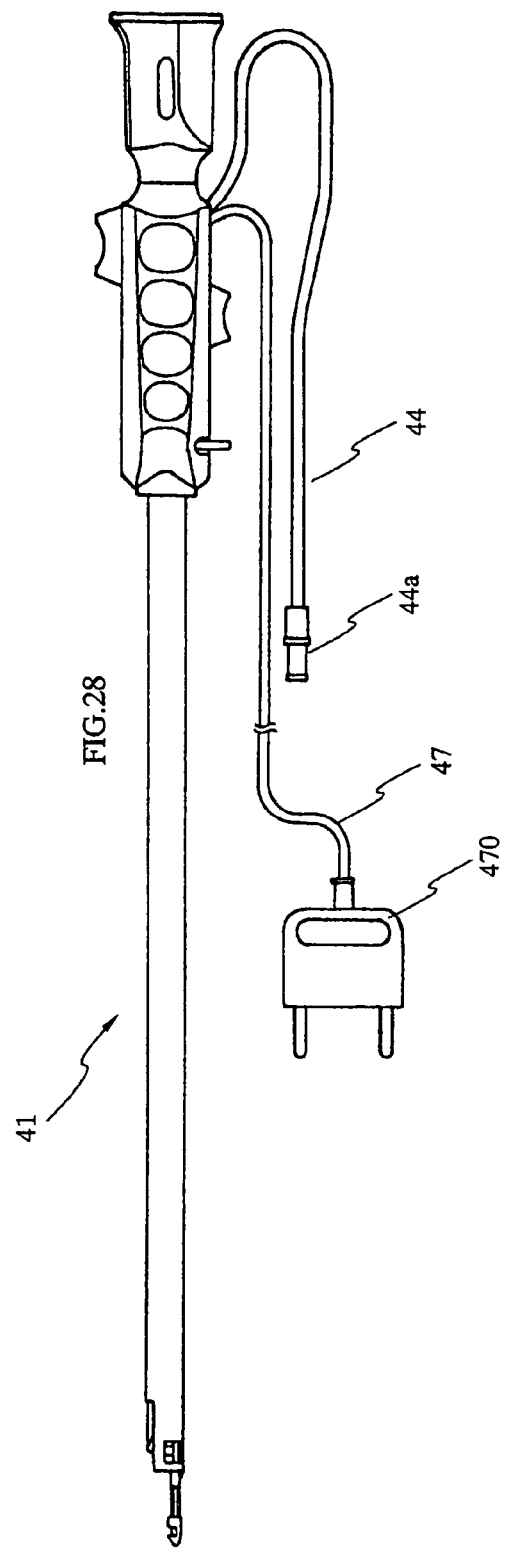

LIVING-BODY TISSUE REMOVING APPARATUS

This application is based upon and claims the benefit of priority from U.S. Provisional Application Ser. No. 60/516,649 filed on Oct. 31,2003, the entire contents of which are incorporated herein by reference.

BACKGROUND OF THE INVENTION

1. Field of the Invention

The present invention relates to a living-body tissue removing apparatus which is used for operation for drawing and removing the subcutaneous vessel by using an endoscope.

2. Description of the Related Art

A method for drawing and removing the subcutaneous vessel by using an endoscope and an apparatus thereof are known.

In the bypass graft surgery of the blood vessel in the heart, the blood vessel of the lower limb is used as the blood vessel for bypass. Conventionally, the operation that the skin of the lower limb is cut and the blood vessel is removed so as to entirely view the blood vessels from the inguinal region of the lower limb to the ankle.

The present invention relates to the living-body tissue removing apparatus used for the above-mentioned operation.

SUMMARY OF THE INVENTION

According to the present invention, a living-body tissue removing apparatus includes, a grip portion, an inserting portion which is connected to the grip portion and is inserted in the body, and an air feed portion which feeds predetermined air into the inserting portion so as to discharge the predetermined air from an opening arranged to the inserting portion.

BRIEF DESCRIPTION OF THE DRAWINGS

FIG. 27 is a diagram showing the appearance of a disposable dissector; FIG. 28 is a diagram showing the appearance of the disposable harvester.

DESCRIPTION OF THE PREFERRED EMBODIMENTS

A description is individually given of an operation method, an operation system, a trocar, a dissector, and a harvester according to the present invention.

(1) Operation Method

Figure 1:
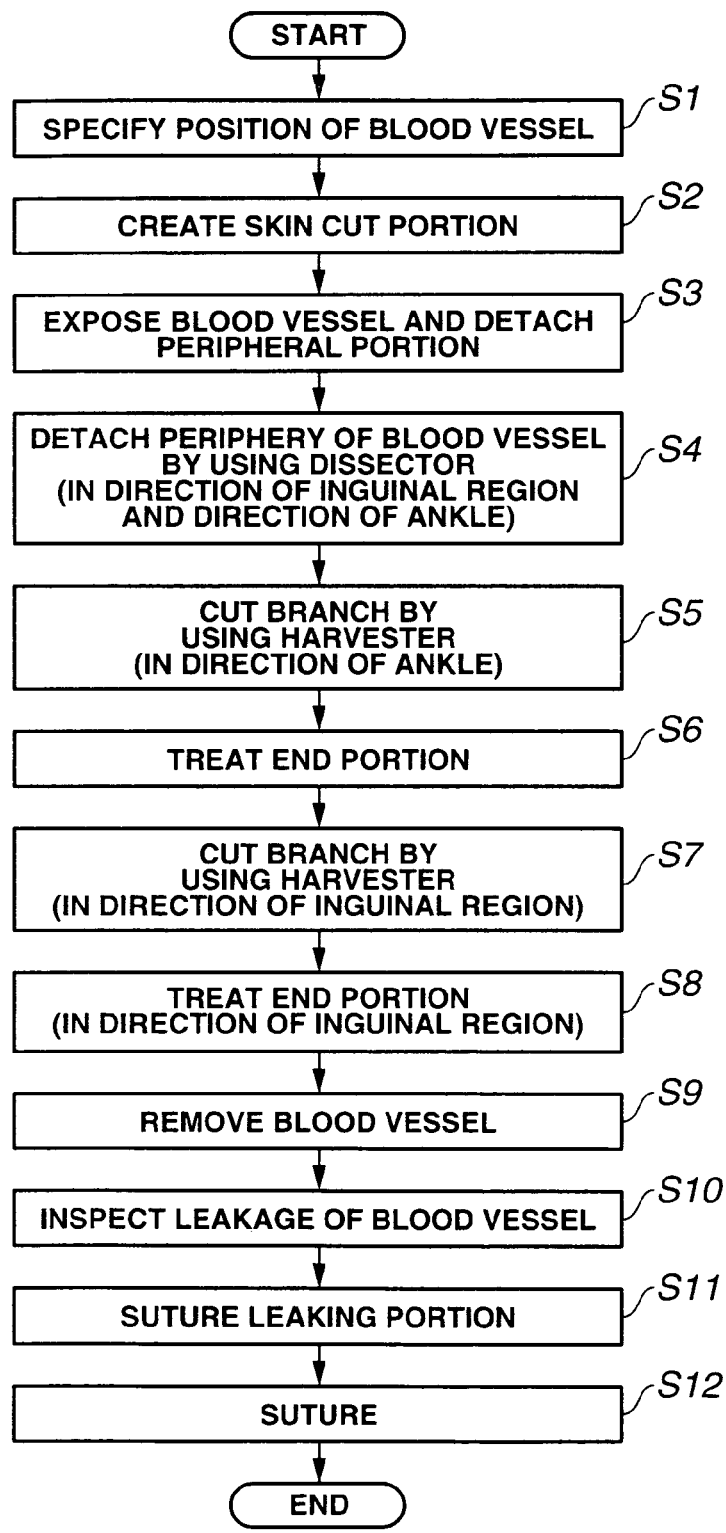
FIG. 1 is a flowchart for explaining an operation method by drawing and removing the subcutaneous vessel.

FIG. 1 is a flowchart for explaining an operation method for drawing and removing the subcutaneous vessel. FIGS. 2 to 6 are diagrams for explaining the operation method. A description is given of the operation method for removing the blood vessel with reference to FIGS. 2 to 6.

In the bypass graft surgery of the heart, the blood vessel of the lower limb is used for the blood vessel for bypass. A description is given of the case of removing the entire length of the great saphenous vein (hereinafter, simply referred to as the blood vessel) from the femoral portion to the ankle of the lower limb as a removing target blood vessel, which is used for the bypass. Later, a description will be given of the detailed structure of a dissector, a trocar, and a harvester as tools used for the removal. The dissector and the harvester are the living-body tissue removing apparatus. Further, an endoscope is inserted in the dissector and the harvester. An operator removes the blood vessel while viewing an endoscope image. The endoscope is rigid, and is connected to a TV monitor via a TV camera head connected to an eyepiece portion, thereby displaying an endoscope image on the screen of the TV monitor. Illuminating light is irradiated from a front end portion of the rigid endoscope, thereby illuminating the subcutaneous tissue and a blood vessel 11.

Figure 2:
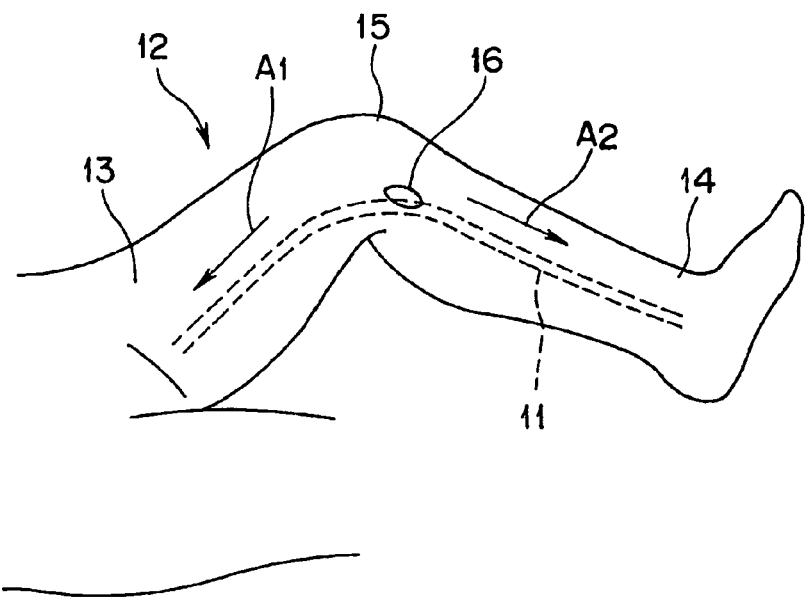
FIGS. 2 to 6 are diagrams for explaining the operation method shown in FIG. 1.

Referring to FIG. 2, a removing target blood vessel 11 exists between an inguinal region 13 of a lower limb 12 and an ankle 14. The removed blood vessel 11 has a length of 60 cm.

First, the operator specifies the position of the blood vessel 11 (step (hereinafter, abbreviated to S) 1). The position of the blood vessel 11 is specified by the operator's tactile sensation or by a device such as a sonar. Next, the operator creates one portion, e.g., a skin cut portion 16 having the length of 2.5 cm of the cutting opening by using a knife slightly under a knee 15 on the top of the specified blood vessel 11 along the direction of the blood vessel 11 (S2). At the skin cut portion 16, the blood vessel 11 is exposed and the tissue around the blood vessel 11 is dissected (S3).

The tissue around the blood vessel 11 over the entire length thereof is dissected by using the dissector (S4). Specifically, the operator sets a trocar 21 to the skin cut portion 16, and passes the dissector through a guide tube portion 22 of the trocar 21. Further, the operator gradually inserts the dissector in the direction (shown by an arrow A1) from the skin cut portion 16 to the inguinal region 13 while viewing the endoscope image, and slowly dissects the blood vessel 11 from the peripheral tissue. The endoscope image is necessary for the operator to dissect the peripheral tissue along the blood vessel 11.

Upon dissecting the peripheral tissue of the blood vessel 11, the skin surface is the up direction of the blood vessel 11 and then the operator dissects the blood vessel 11 in the up and down directions thereof, and further dissects the blood vessel 11 in the left and right directions thereof, thereby completely dissecting the peripheral tissue along the entire circumference of the blood vessel 11. By dissecting the peripheral tissue throughout the entire circumference of the blood vessel 11, the branch of the blood vessel 11 is preferably viewed in the endoscope image.

Upon ending the dissection of the peripheral tissue of the blood vessel 11 in the direction of the inguinal region 13, the dissector is taken out from the trocar. The direction of the trocar of the skin cut portion 16 is changed, the dissector is gradually inserted in the direction (shown by an arrow A2) of the ankle 14 from the skin cut portion 16, and the blood vessel 11 is dissected from the peripheral tissue while viewing the endoscope image.

Figure 3:
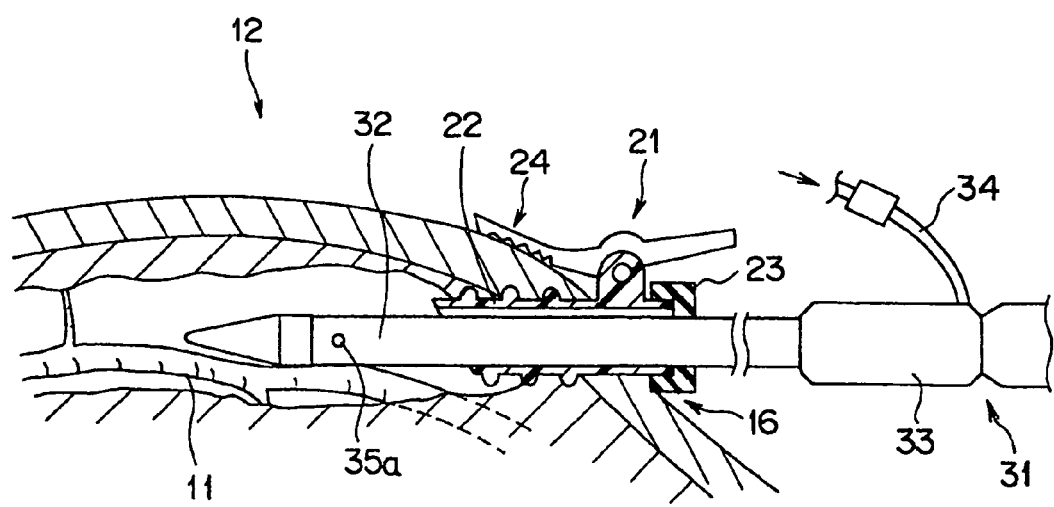

FIG. 3 is a cross-sectional view showing the state in which the dissector is inserted subcutaneously under the lower limb 12 via the trocar 21 from the skin cut portion 16 in the direction of the inguinal region 13. The trocar 21 comprises: a cylindrical guide tube portion 22 for inserting an inserting portion 32 of a dissector 31; a sealing portion 23; and a fixing portion 24 for fixing the dissector to the skin. Upon setting the trocar 21 to the skin cut portion 16, the guide tube portion 22 is inserted in the direction of the inguinal region from the skin cut portion 16, and is fixed to the skin by the fixing portion 24. The inserting portion 32 of the dissector 31 is inserted subcutaneously under the skin of the lower limb 12 via the guide tube portion 22 of the trocar 21 fixed to the skin cut portion 16 by using the fixing portion 24. As will be described later, an endoscope inserting portion is inserted in an inserting portion 32. Since the inserting direction of the dissector 31 is along the direction of the blood vessel 11, the operator gradually inserts the dissector so as to dissect the peripheral tissue of the blood vessel 11 therefrom while viewing the endoscope image. That is, the inserting operation is not suddenly performed under the inguinal region 13 along the blood vessel 11 from the skin cut portion 16. By advancing and returning the dissector 31 along the inserting direction, the portion of blood vessel 11 to the inguinal region 13 is gradually dissected and further the portion of the blood vessel 11 to the ankle 14 is dissected.

In this case, the gas of, e.g., carbon dioxide is fed from an air feed tube 34 connected to a grip portion 33 of the dissector 31 by using an air feed function arranged to the dissector 31. The gas is discharged from an opening 35a arranged to a front end portion of the inserting portion 32. The blood vessel 11 is dissected from the peripheral tissue thereof, and the gas of carbon dioxide exists between the dissected tissue and the blood vessel. Therefore, the field of the endoscope operation is wide, the visible recognition is improved, and the operator easily performs the dissecting operation.

Next, the dissector 31 is taken out from the trocar 21. The trocar 21 is in the same state and a harvester is inserted. Further, the branch of the blood vessel 11 is cut from the skin cut portion 16 to the ankle 14 (S5).

A branch 11a is cut by inserting a harvester 41 from the skin cut portion 16 to the down side of the ankle 14 and by cutting the branch 11a of the blood vessel 11 one by one to the skin cut portion 16 from the ankle 14.

A bipolar cutter 43 as an electric knife arranged to a front end portion of the inserting portion 42 of the harvester 41 cuts the branch 11a. The branch 11a cut by the bipolar cutter 43 has a cut portion at which the bleeding almost stops. The entire branch 11a of the blood vessel 11 is cut to the ankle 14 by using the harvester 41.

Although the structure of the harvester 41 will be described later, it is briefly described here. The blood vessel 11 is hooked to a vein keeper 45 as a blood vessel keeping portion arranged to the front end of the harvester 41. Upon hooking the blood vessel 11 to the vein keeper 45, the vein keeper 45 of the harvester 41 has a mechanism for opening a part of the vein keeper 45, hooking the blood vessel 11 to the opened portion, and closing the part of the opened portion after the hooking operation. Further, the vein keeper 45 is movable in the axial direction of the harvester 41, and the harvester 41 is moved in the direction in the apart direction of the vein keeper 45 from the front end portion of the endoscope. Therefore, the hooked blood vessel 11 is easily viewed in the endoscope image.

The bipolar cutter 43 has, at the front end portion thereof, a groove having the width of 0.5 mm. Upon cutting the branch 11a, the branch 11a is inserted in the groove to be pressed in the groove, thereby cutting the branch 11a in the compressing state. Further, the harvester 41 has, at the front end thereof, a wiper for wiping the deposit attached to a window portion of the front end portion of the rigid endoscope on the inside thereof surrounded by a wiper guarding portion. A part of the cylindrical-shaped wiper guarding portion has a sweeping hole for sweeping the deposit wiped by the wiper. The deposit includes the blood, the fat, and the smoke generated by the electric knife.

The harvester 41 has an air feed function. The gas of, e.g., carbon dioxide is fed from an air feed tube 44 connected to a grip portion 400 of the harvester 41. The gas of carbon dioxide is discharged from an opening (not shown) arranged to the front end portion of the inserting portion 42. Therefore, the cutting operation of the branch 11a of the blood vessel 11 becomes easy.

Incidentally, since a plurality of branches 11a exist at the blood vessel 11, the operator operates the vein keeper 45 at the front end portion of the harvester 41 and holds the blood vessel 11 while viewing the endoscope image at the front end of the inserting portion 42 in the harvester 41. Further, the operator cuts the branch 11a by the bipolar cutter 43 while checking the branches 11a one by one. The structure of the vein keeper 45 will be described in detail later.

A small skin-cut-portion having the length of the cutting opening of 1 cm or less is formed in the ankle 14. The end portion of the blood vessel 11 is drawn from a skin cut portion 17. A thread is taken to the drawn blood vessel or forceps are arranged to the blood vessel 11. Thus, the end portion is treated (S6). In this case, the harvester 41 near the skin cut portion 16 is inserted under the skin of the ankle 14 again. The operator grips the blood vessel 11 by using the forceps while viewing the blood vessel 11 under the skin of the skin cut portion 17 and the forceps. Then, the blood vessel 11 is drawn from the skin cut portion 17.

Figure 4:
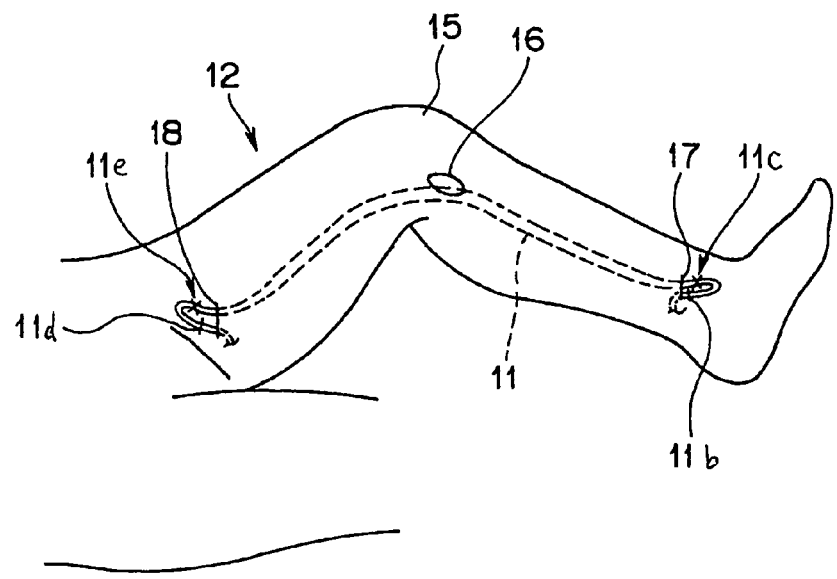

FIG. 4 is a diagram for explaining the treatment of the end portion of the blood vessel 11. In the treatment of the end portion of the blood vessel 11, a part of the blood vessel 11 is knotted by a suture and the blood vessel 11 is cut at a position 11c on the side of the knee 15 rather than a knot 11b. Then, the operator performs the skin cut operation at the skin cut portion 17 by closing the skin cut portion 17 with a tape or something like that.

The harvester 41 is taken out from the trocar 21. The direction of the guide tube portion 22 of the trocar 21 at the skin cut portion 16 is changed to the direction of the inguinal region 13. The harvester 41 is inserted and the branch 11a of the blood vessel 11 is cut from the skin cut portion 16 to the inguinal region 13 (S7). As mentioned above in S6, the operator cuts the branch 11a of the blood vessel 11 from the skin cut portion 16 to the inguinal region 13 while viewing the endoscope image.

Upon cutting the branch 11a, the harvester 41 is first inserted under the inguinal region 13 from the skin cut portion 16, and the branches 11a of the blood vessel 11 are cut one by one from the inguinal region 13 to the skin cut portion 16.

Figure 5:
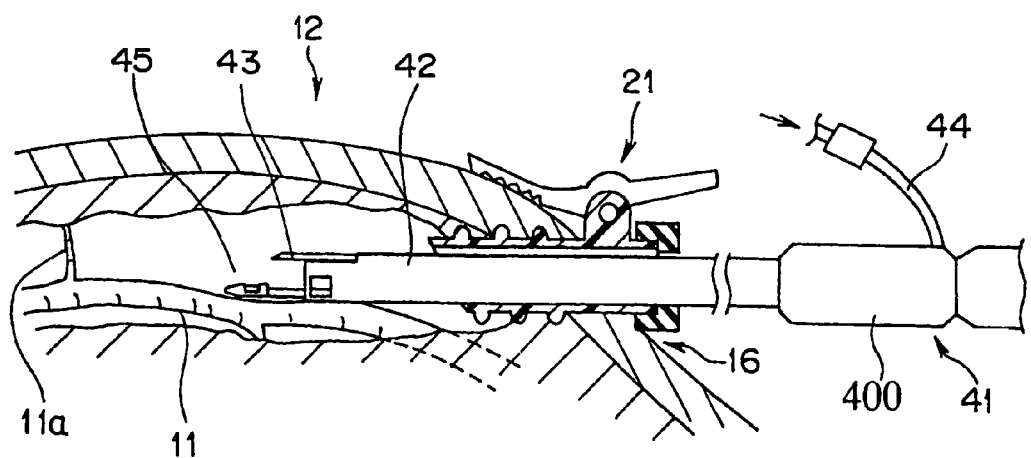

FIG. 5 is a cross-sectional view showing a state in which the harvester is inserted under the skin of the lower limb 12 via the trocar 21 from the skin cut portion 16. The inserting portion 42 of the harvester 41 is inserted under the skin of the lower limb 12 via the guide tube portion 22 of the trocar 21 fixed to the skin cut portion 16 by the fixing portion 24. As will be described later, the endoscope inserting portion is inserted in the inserting portion 42. The harvester 41 is inserted along the direction of the blood vessel 11 and therefore the operator cuts the branches 11a of the blood vessel 11 while viewing the endoscope image.

Upon ending the cut operation of the branches 11a of the blood vessel 11, referring to FIG. 4, a small skin-cut portion having the length of the cutting opening of 1 cm or less is formed in the inguinal region 13. The end portion of the blood vessel 11 is drawn from a skin cut portion 18. A suture is taken to the drawn blood vessel or forceps are arranged to the blood vessel 11. Thus, the end portion is treated (S8). In this case, the harvester 41 near the skin cut portion 16 is inserted again under the skin of the inguinal region 13. The operator holds the blood vessel 11 by using the forceps while viewing the forceps and the blood vessel 11 under the skin of the skin cut portion 18. Then, the blood vessel 11 is drawn from the skin cut portion 18. As treated at the skin cut portion 17 of the ankle 14, the end portion of the blood vessel 11 is treated by knotting a part of the blood vessel 11 with the suture and by cutting the blood vessel 11 at a position 11e on the knee 15 side rather than a knot 11d. The skin cut portion 18 is then cut by closing the skin cut portion 18 by the operator with the tape.

Figure 6:
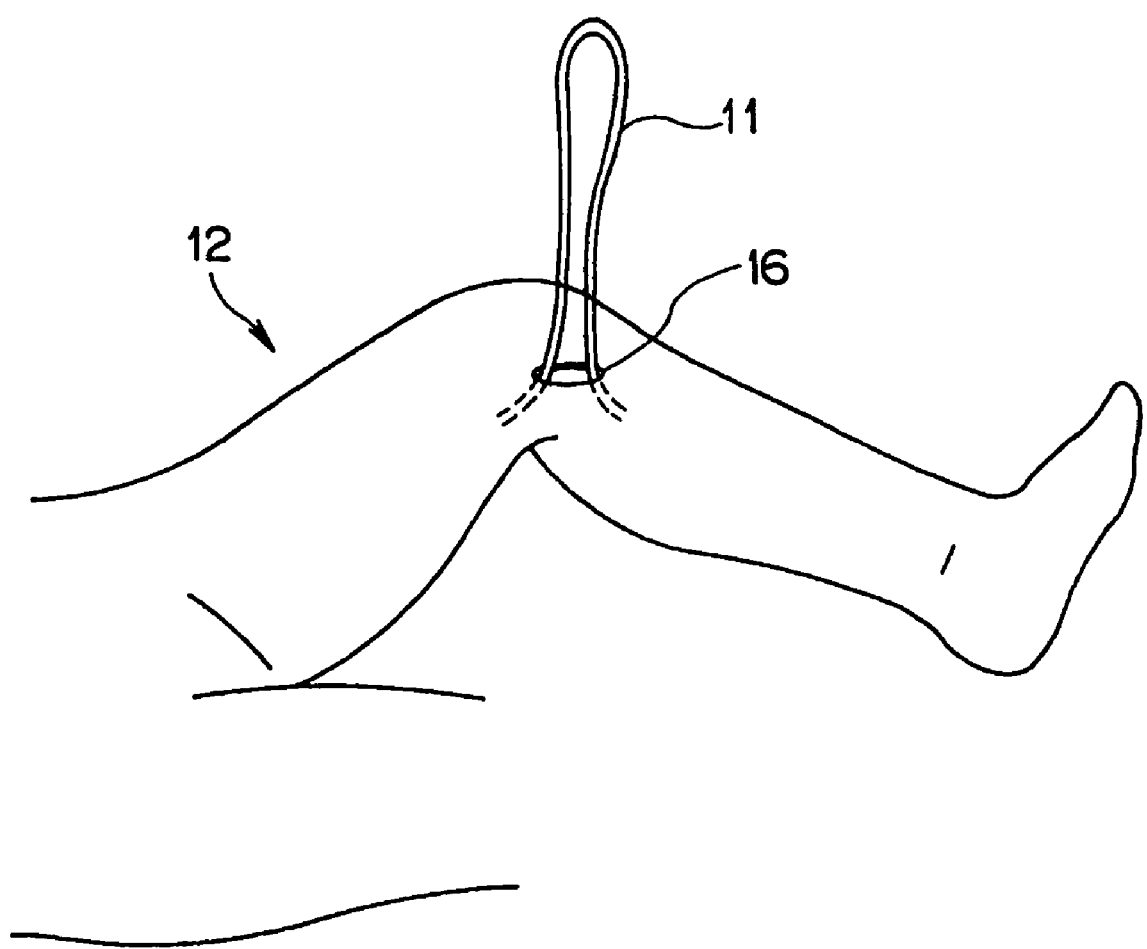

Referring to FIG. 6, the operator removes the blood vessel 11 of 60 cm from the skin cut portion 16 (S9). FIG. 6 is a diagram for explaining the state for removing the blood vessel 11 from the skin cut portion 16. Upon ending the removal of the blood vessel 11, any hole is opened at the removed blood vessel 11 and then since the blood vessel 11 in this case is not used as the blood vessel for bypass. Therefore, the operator inspects the leakage of the blood vessel 11 (S10).

In the state in which the entire branches 11a are knotted, a syringe is attached to one end of the blood vessel 11 in consideration of the valve direction of the blood vessel 11. Then, the physiological saline solution is flowed in the blood vessel 11. The operator inspects the leakage of the blood vessel 11 depending on whether or not a hole for flowing out the physiological saline solution exists. Further, the operator knots the entire branches 11a of the blood vessel 11 to prevent the leakage of the blood from the end of the branch 11a whose end is cut.

If the hole for leaking the physiological saline solution exists, the hole at the portion is sutured (S11). Finally, the skin cut portion 16 is sutured (S12).

As compared with the conventional operation in which the tissue at a predetermined portion of the lower limb 12 is incised so as to entirely view the blood vessel 11 from the inguinal region 13 of the lower limb 12 to the ankle 14, the above-mentioned method for removing the blood vessel using the endoscope has the low invasiveness for the patient because the number of skin cut portions is three. For example, the time until the patient can walk after the operation may be able to be reduced.

(2) Operation System

Figure 7:
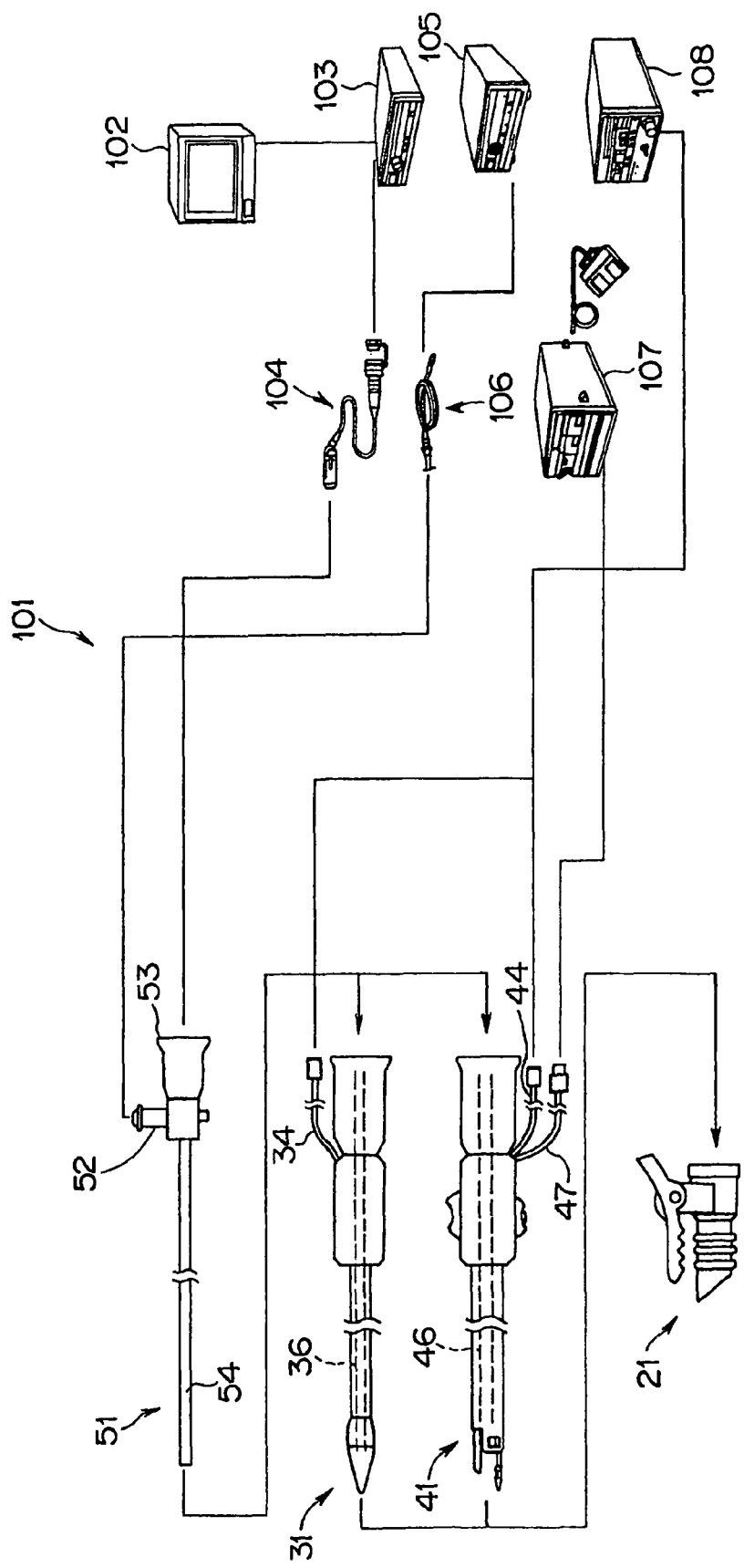
FIG. 7 is a structure diagram showing the structure of an operation system comprising an apparatus and a tool used for the operation.

FIG. 7 is a structure diagram showing the structure of an operation system comprising an apparatus and a tool used for the above-mentioned operation. An operation system 101 comprises: the trocar 21; the dissector 31; the harvester 41; and a rigid endoscope 51. The operation system 101 further comprises: a TV monitor 102 as a display device; a camera control unit (hereinafter, referred to as a CCU) 103; a TV camera device 104; a light source device 105; a light guide cable 106; an electric knife device 107; and an air feed device 108.

One end of the light guide cable 106 is connected to a light guide connector portion 52 of the rigid endoscope 51. Another end of the light guide cable 106 is connected to the light source device 105. The light from the light source device 105 is supplied to the rigid endoscope 51 via the light guide cable 106 in which a light guide of an optical fiber is inserted. The subject is illuminated with light from the front end portion of the rigid endoscope 51. A TV camera head portion of the TV camera device 104 is connected to an eyepiece portion 53 on the base end side of the rigid endoscope 51. The TV camera device 104 is connected to the CCU 103, and the image of the subject captured by the rigid endoscope 51 is displayed on the screen of the connected TV monitor 102.

An inserting portion 54 at the front end of the rigid endoscope 51 is inserted in a rigid-endoscope inserting channel 36 of the dissector 31 from the base end side of the dissector 31. Similarly, the inserting portion 54 at the front end of the rigid endoscope 51 is inserted in a rigid-endoscope inserting channel 46 of the harvester 41 from the base end side of the harvester 41.

The air feed tube 34 of the dissector 31 is connected to the air feed device 108, and the gas of, e.g., carbon dioxide is fed from the air feed device 108 to the air feed tube 34. Further, the gas of carbon dioxide is discharged from the opening 35a as the air feed port.

The air feed tube 44 of the harvester 41 is further connected to the air feed device 108, and the gas of, e.g., carbon dioxide is fed from the air feed device 108 to the air feed tube 44. Further, the gas of the carbon dioxide is discharged from an opening (not shown in FIG. 7) as an air feed port.

The harvester 41 has an electric cable 47 for the bipolar cutter 43. A connector arranged to the base end side of the electric cable 47 connects the harvester 41 to the electric knife device 107.

The operator performs the above-mentioned operation by using the operation system 101 having the above-mentioned structure.

(3) Trocar

Figure 8A:
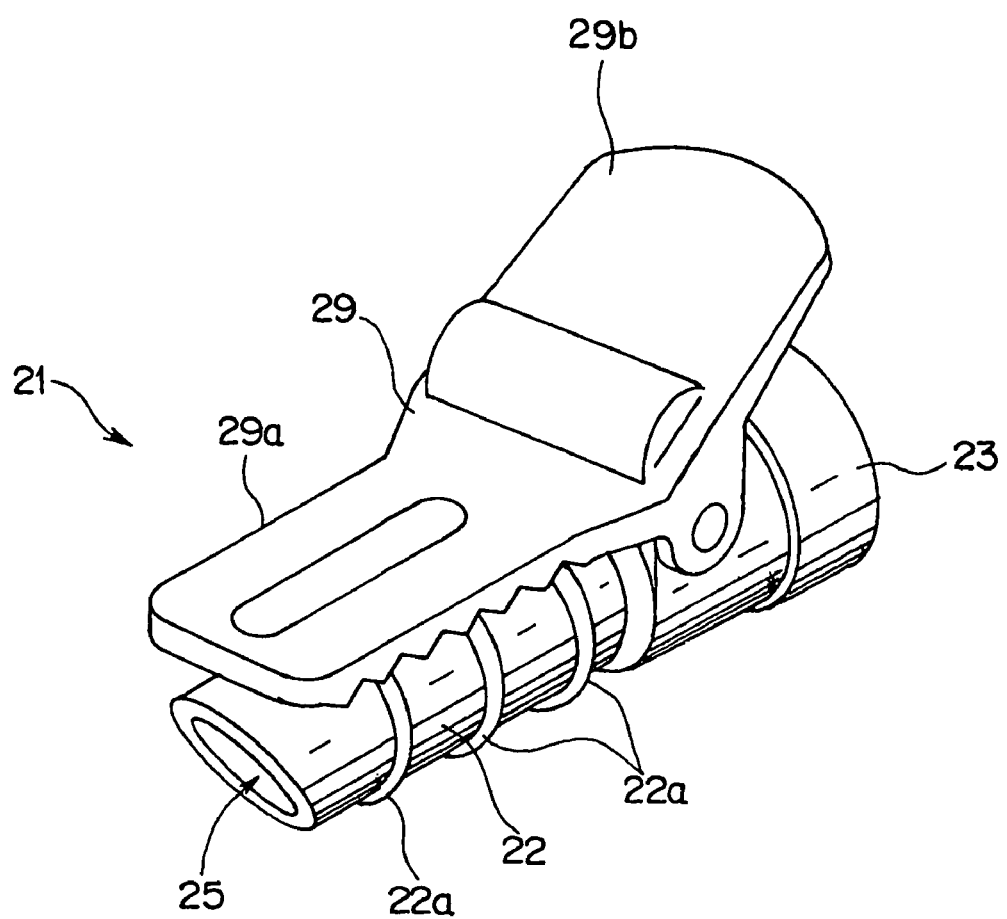
FIG. 8A is a perspective view showing a trocar.
Figure 8B:
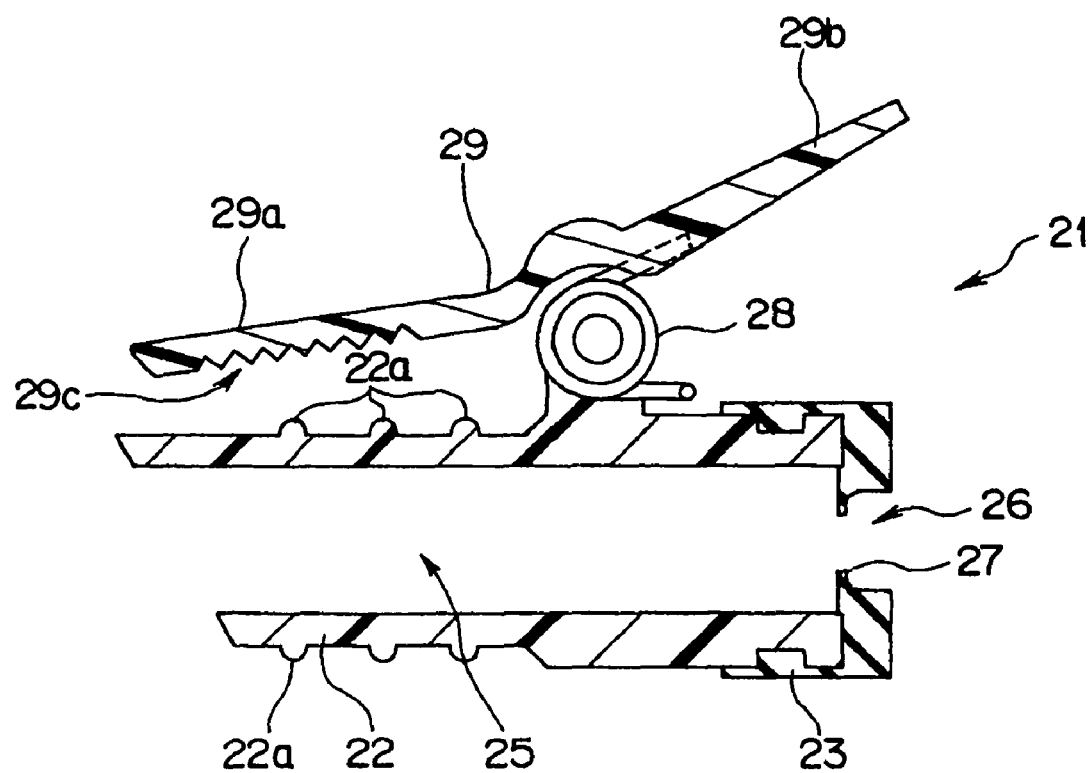
FIG. 8B is a longitudinal cross-sectional view showing the trocar.

FIG. 8A is a perspective view showing the trocar 21. FIG. 8B is a longitudinal cross-sectional view showing the trocar 21. The trocar 21 comprises: the guide tube portion 22 as a guide sheath; the sealing member 23; and the fixing portion 24 for fixing to the skin. The guide tube portion 22 has a cylindrical hollow portion 25 for inserting the inserting portions 32 and 42 of the dissector 31 and the harvester 41. The front end side of the guide tube portion 22 is shaped like being cut at a predetermined angle, e.g., an angle of 45° in the direction perpendicular to the axial direction of the guide tube portion 22. The base end side of the guide tube portion 22 is shaped like being cut in the direction perpendicular to the axial direction of the guide tube portion 22. Further, the base end side of the guide tube portion 22 has the sealing member 23. The sealing member 23 contains an elastic member, and has a hole 26 having a inner diameter on the front end side, smaller than that of the guide tube portion 22. A projected portion 27 is arranged onto the inner peripheral surface of the hole 26 on the front end side so that the inner diameter on the front end side is smaller than that on the base end side. The above-shaped hole 26 sets, to the airtight state under the skin, the inserting portion 32 or 42 of the dissector 31 or the harvester 41 inserted in the guide tube portion 22.

A clipping member 29 using the elastic force of a torsion spring 28 as an elastic member is arranged to the outer periphery of the guide tube portion 22 of the trocar 21. The clipping member 29 serving as a fixing member comprises a front end portion 29a and a base end portion 29b and is plate-shaped with downturning of the corners. The torsion spring 28 is arranged in the middle of the plate-shaped portion which is bent with downturning of the corners.

The torsion spring 28 always presses the front end portion 29a of the clipping member 29 to the outer circumferential surface of the guide tube portion 22. The base end portion 29b of the clipping member 29 is pressed down against the pressing force of the torsion spring 28 and thus the front end portion 29a is detached from the outer circumferential surface of the guide tube portion 22. The skin or the like of the lower limb 12 is sandwiched between the front end portion 29a of the clipping member 29 and the outer circumferential surface of the guide tube portion 22 by pressing down the base end portion 29b of the clipping member 29 to the side of the outer circumferential surface of the guide tube portion 22. Here, in place of the torsion spring 28, a plate spring may be used and the elastic force of the plate spring may be used to sandwich the skin or the like of the lower limb 12.

The plurality of circular projected portions 22a are circumferentially arranged to the outer circumferential surface of the guide tube portion 22. The projected portions 22a may be arranged integrally with the guide tube portion 22, or may be arranged separately from the guide tube portion 22. Facing to the outer peripheral surface side of the guide tube portion 22, an engaging portion 29c is formed on the front end portion 29a of the clipping member 29. As shown in FIGS. 3 and 4, in the state in which the skin or the like of the lower limb 12 is sandwiched by the pressing force of the torsion spring 28 between the front end portion 29a of the clipping member 29 and the outer circumferential surface of the guide tube portion 22, the skin or the like of the lower limb 12 is certainly sandwiched and is fixed by the engaging portion 29c of the clipping member 29 and the outer circumferential surface of the guide tube portion 22. Therefore, the engaging portion 29c of the clipping member 29 and the engaging portion 22a of the guide tube portion 22 form the fixing portion 24 having a so-called non-slip mechanism.

FIGS. 9A to 9E are diagrams showing examples of the surface shape of the engaging portion 29c of the clipping member 29 facing toward the guide tube portion 22.

Figure 9A:
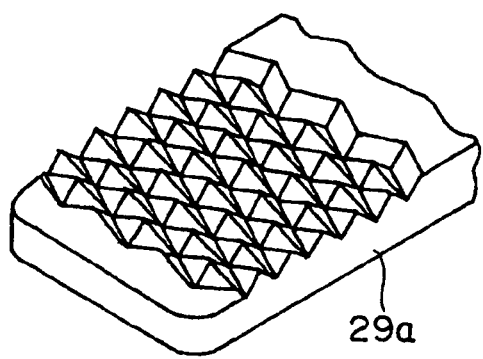
FIGS. 9A to 9E are diagrams showing examples of the surface shape on a guide tube portion at an engaging portion of a clip member.

FIG. 9A is a diagram showing the example of the surface shape of the engaging portion 29c of the clipping member 29, which is obtained by forming two intersectional triangular grooves. Referring to FIG. 9A, the surface of the engaging portion 29c has a plurality of triangular pyramids.

Figure 9B:
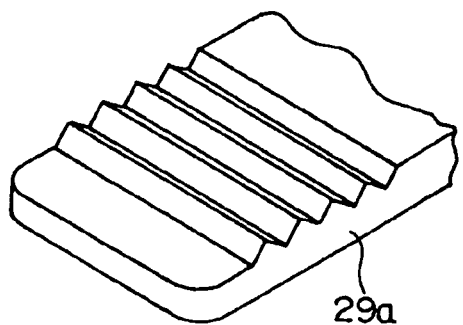

FIG. 9B is a diagram showing the example of the surface shape, in which the cross section in the direction perpendicular to the axial direction of the front end portion 29a of the clipping member 29 has a plurality of groove shapes like isosceles triangle. Referring to FIG. 9B, the surface of the engaging portion 29c is shaped by forming a plurality of triangular grooves in the direction perpendicular to the axial direction of the front end portion 29a of the clipping member 29.

Figure 9C:
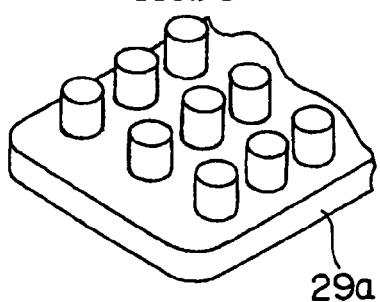

FIG. 9C is a diagram showing the example of the surface shape, having a plurality of projected portions on the surface of the engaging portion 29c of the clipping member 29. Referring to FIG. 9C, the surface of the engaging portion 29c has a plurality of cylindrical projected portions.

Figure 9D:
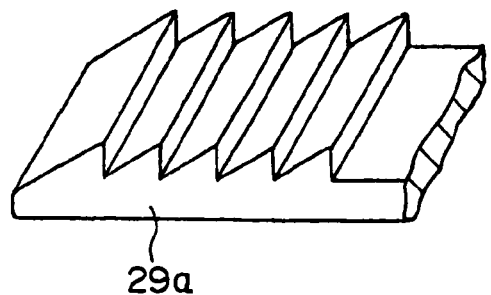

FIG. 9D is a diagram showing the example of the cross section having a plurality grooves of right-angled triangle in the direction perpendicular to the axial direction of the front end portion 29a of the clipping member 29. Referring to FIG. 9D, the surface of the engaging portion 29c has a plurality of triangular grooves having a surface portion perpendicular to the axial direction of the front end portion 29a and a surface portion at a predetermined angle to the axial direction of the front end portion 29a.

Figure 9E:
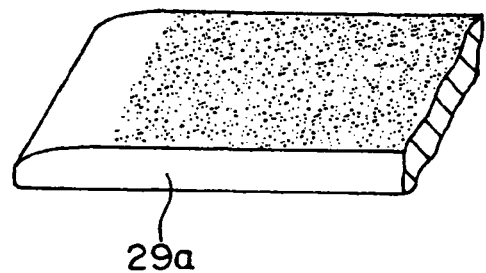

FIG. 9E is a diagram showing the example of the surface shape of the engaging portion 29c of the clipping member 29, being finished coarsely. Referring to FIG. 9E, the surface of the engaging portion 29c is like a rasping surface. The coarseness of the rasping surface is about No. 30.

The above-mentioned surface may be shaped integrally with the front end portion 29a of the clipping member 29. Or, it may be shaped separately from the clipping member 29.

(4) Dissector

Figure 10:
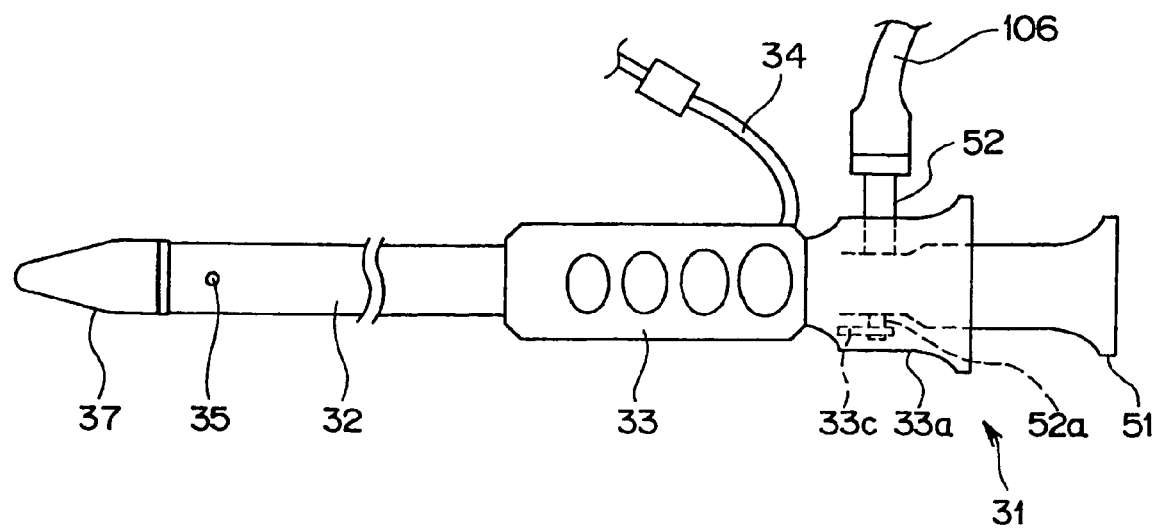
FIG. 10 is a side view showing a dissector.

FIG. 10 is a side view showing the dissector 31. A dissecting member 37 is arranged at the front end of the metallic inserting portion 32 of the dissector 31 serving as the living-body tissue removing apparatus. The dissecting member 37 contains transparent resin, is cylindrical-shaped on the base end side, and is conically shaped on the front end side. The dissecting member 37 is a transparent member and therefore, upon inserting the dissecting member 37 under the skin, it is possible to obtain, by the rigid endoscope 51, the subject image illuminated by the illuminating light from the front end portion of the rigid endoscope 51 inserted in the rigid-endoscope inserting channel 36. The rigid-endoscope inserting channel 36 has an endoscope inserting portion for inserting a rigid endoscope 51 in the inserting portion of the dissector 31.

Figure 11:
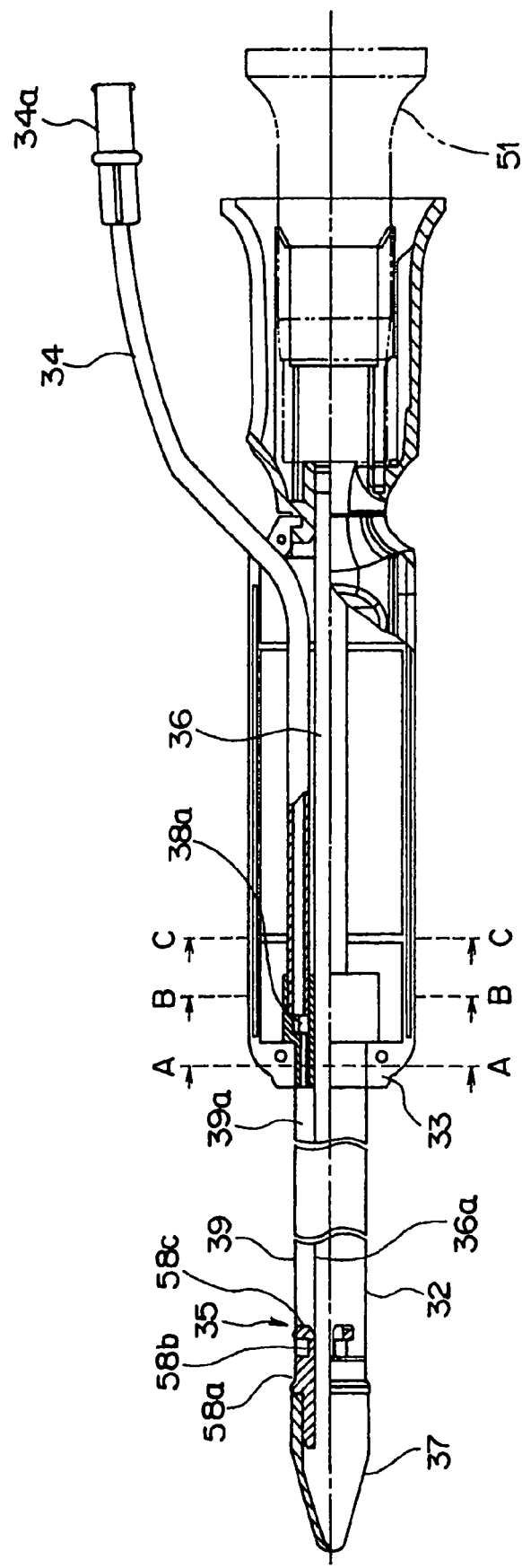
FIG. 11 is a partial cross-sectional view showing the dissector.
Figure 12A:
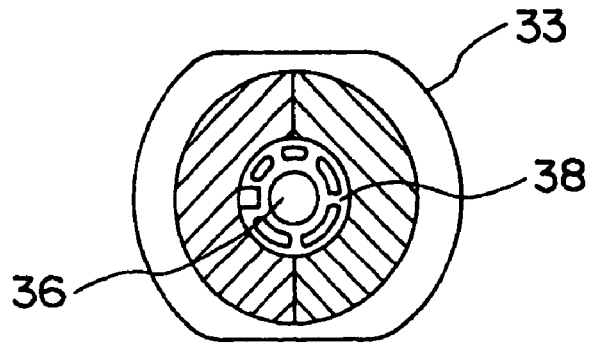
FIGS. 12A to 12C are cross-sectional views along A-A, B-B, and C-C lines shown in FIG. 11, respectively.
Figure 12B:
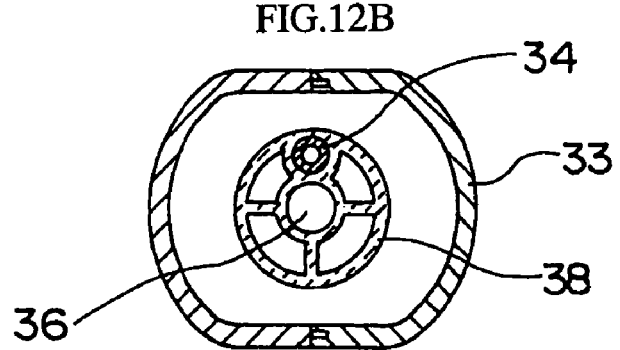
Figure 12C:
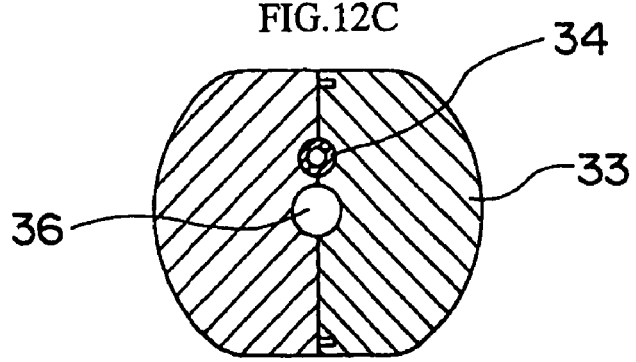

FIG. 11 is a partial cross-sectional view showing the dissector 31. FIGS. 12A to 12C are cross-sectional views along A-A, B-B, and C-C lines in FIG. 11, respectively. A metallic tube member 36a having the rigid-endoscope inserting channel 36 is inserted along the axial direction of the dissector 31 therein from the base end side of the grip portion 33 to the front end portion of the inserting portion 32. A first connecting member 38 is arranged on the front end side of the grip portion 33. A sheath 39 of the inserting portion 32 is fit into the front end side of the first connecting member 38. Further, the front end side of the grip portion 33 is fit into the front end side of the first connecting member 38. The first connecting member 38 comprises a hole 38a communicating an inner space of the grip portion 33 with the inner space of the metallic sheath 39. The air feed tube 34 is fit into the grip portion 33 at one end of the hole 38a. Another end of the hole 38a is opened in an outer space 39a of a tube member 36a in the metallic sheath 39. An air feed connector 34a is arranged at the base end of the air feed tube 34. The air feed connector 34a is connected to a connector of the tube connected to the air feed device 108.

The dissecting member 37 is connected to the sheath 39 of the inserting portion 32 by a second connecting member 58a. The dissecting member 37 is fit into the front end side of the second connecting member 58a, and the sheath 39 is fit into the base end side of the second connecting member 58a. Thus, the dissecting member 37 is airtightly connected to the sheath 39.

Three coronoid portions 58b are formed on the base end side of the second connecting member 58a. A front end of a coronoid portion 58b has a projected portion 58c directed to the radiating direction from the central axis on the plane perpendicular to the axial direction of the inserting portion 32. The sheath 39 has the holes 35 at the positions corresponding to the front end portions of the three coronoid portions 58b. The hole of the sheath 39 in the inserting portion 32 is formed so as to engage the projected portions 58c to the holes 35. The dimensions of the projected portion 58c and the holes 35 are set so as to form a space between the holes 35 and the projected portion 58c while the projected portion 58c are engaged to the holes 35, thereby forming three openings 35a. The outer diameter of the second connecting member 58a on the base end side is larger than the outer diameter of the sheath 39.

The gas of carbon dioxide fed from the air feed tube 34 is introduced in a sealed space 39a formed by the first connecting member 38, the second connecting member 58a, the sheath 39, and the tube member 36a via the first connecting member 38. The introduced gas is discharged to the outside of the inserting portion 32 via the openings 35a from the sealed space 39a. The air feed tube 34 has an air feed portion which feeds the gas of carbon dioxide in the inserting portion of the dissector 31, and further has a discharge port to the outside of the inserting portion 32 from the opening 35a.

Figure 13:
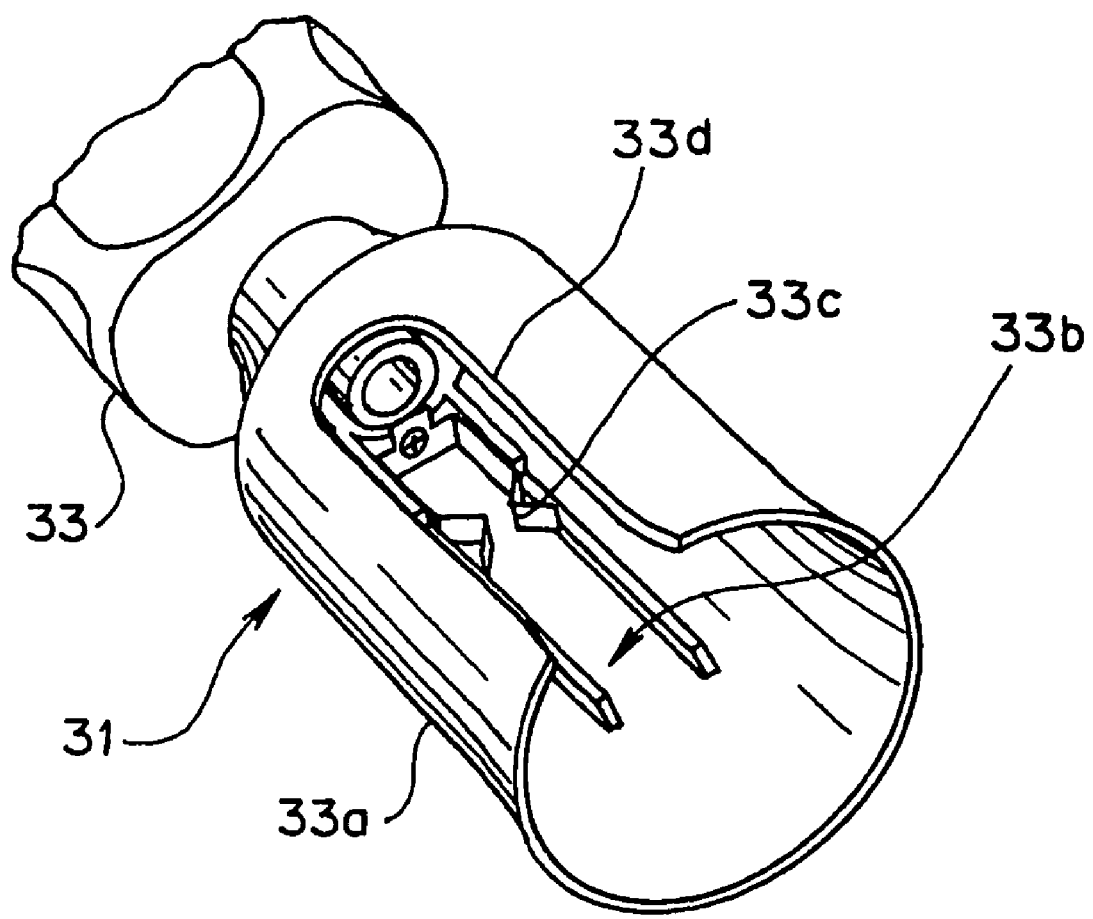
FIG. 13 is a partial perspective view showing the dissector from a base end side thereof.

FIG. 13 is a partial perspective view showing the dissector 31 from the base end side. Referring to FIG. 13, in order to easily and certainly fix the rigid endoscope 51 to the base end portion of the dissector 31, a guide groove 33b is arranged along the axial direction of the dissector 31 on the inner peripheral surface of a base end portion 33a of the dissector 31. Further, a fixing member 33c is fixed to the guide groove 33b by a screw. The fixing member 33c is formed by bending a metallic plate-shaped member like being U-shaped. Both end portions like being U-shaped are bent to have projected portions directed to the inside of the U-shape. A projected portion 52a is arranged on the front end side of the eyepiece portion 53 in the rigid endoscope 51.

A notch portion 33d is arranged to the base end portion 33a, and the light guide connector portion 52 is moved along the notch portion 33d.

Upon inserting the rigid endoscope 51 from the base end portion of the dissector 31, the rigid endoscope 51 is inserted to the base end portion of the dissector 31 so that the projected portion 52a enters the dissector 31 along the guide groove 33b arranged to the inner peripheral surface of the base end portion 33a and the light guide connector portion 52 enters it along the notch portion 33d. The rigid endoscope 51 is inserted from the base end portion of the dissector 31, then, the projected portion 52a is moved along the inside of the guide groove 33b, and the projected portion 52a is over the projected portion of the metallic fixing member 33c against the elastic force of the fixing member 33c. In this case, the light guide connector portion 52 is moved along the notch portion 33d arranged to the base end portion 33a.

Therefore, upon inserting the rigid endoscope 51 from the base end portion of the dissector 31, the positional relationship between the dissector 31 and the rigid endoscope 51 is set so that the light guide connector portion 52 enters the notch portion 33d and the projected portion 52a enters the guide groove 33b. After that, the rigid endoscope 51 is inserted in the dissector 31. The rigid endoscope 51 is inserted in the dissector 31, then, the projected portion 52a of the rigid endoscope 51 is engaged and fixed in the halfway in such a manner that it is sandwiched by the fixing member 33c, and the elastic force of the fixing member 33c prevents the easy pulling-out operation of the rigid endoscope 51.

Upon engagement and fixing, the clicking noise is generated between the engaged rigid endoscope 51 and the dissector 31. Therefore, the user confirms the setting by the clicking noise.

Figure 30:
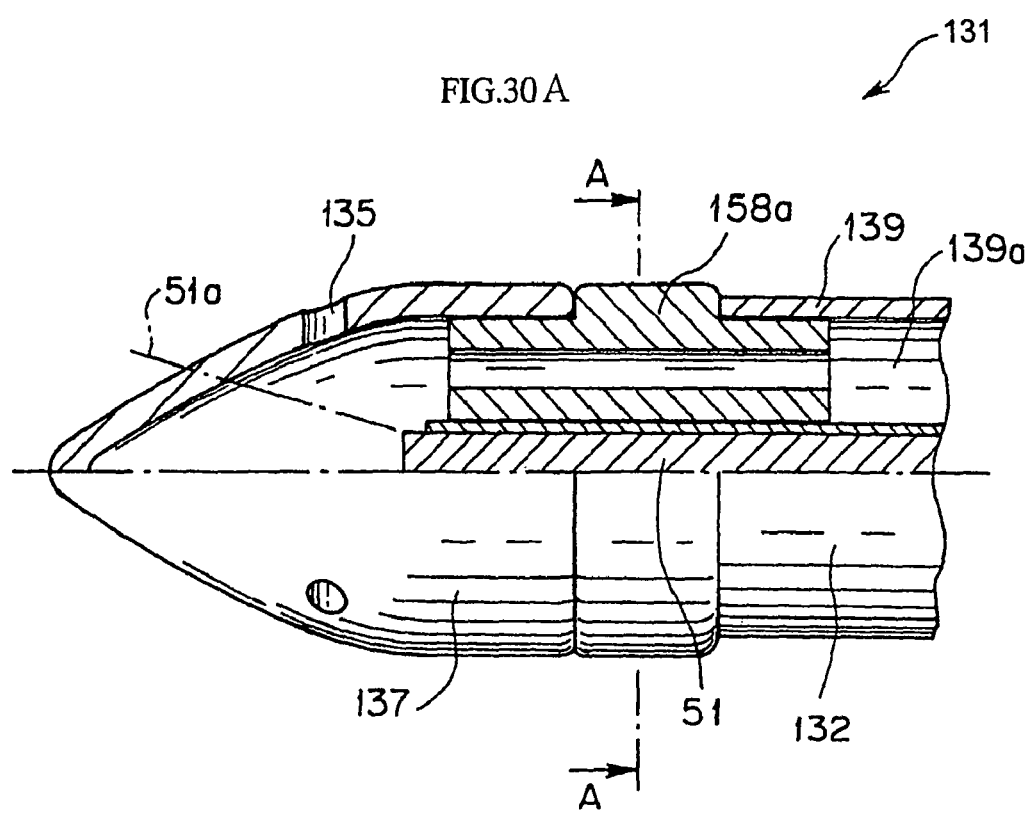
FIGS. 30A to 31C are diagrams for explaining a front end portion of the dissector according to modifications.
Figure 30B:
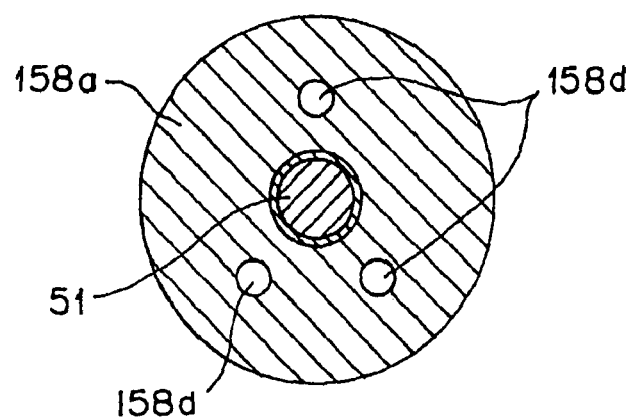

FIGS. 30A to 31B are diagrams for explaining the front end portion of a dissector according to modifications. FIGS. 30A and 30B are diagrams according to a first modification. FIG. 30A is a cross-sectional view showing the front end portion of a dissector 131. FIG. 30B is a cross-sectional view along an A-A line in FIG. 30A.

Referring to FIG. 30A, a second connecting member 158a is engaged into a sheath 139, thereby forming a sealed space 139a. The second connecting member 158a has a plurality of air holes 158d communicated with the inside of a dissecting member 137 from a sealed space 139a. The dissecting member 137 has a hole 135 at the area except for the area within a field-of-view angle 51a of the rigid endoscope 51 inserted in the dissector 131.

The gas introduced to the sealed space 139a is discharged to the outside of an inserting portion 132 via the air holes 158d and the hole 135.

Figure 31A:
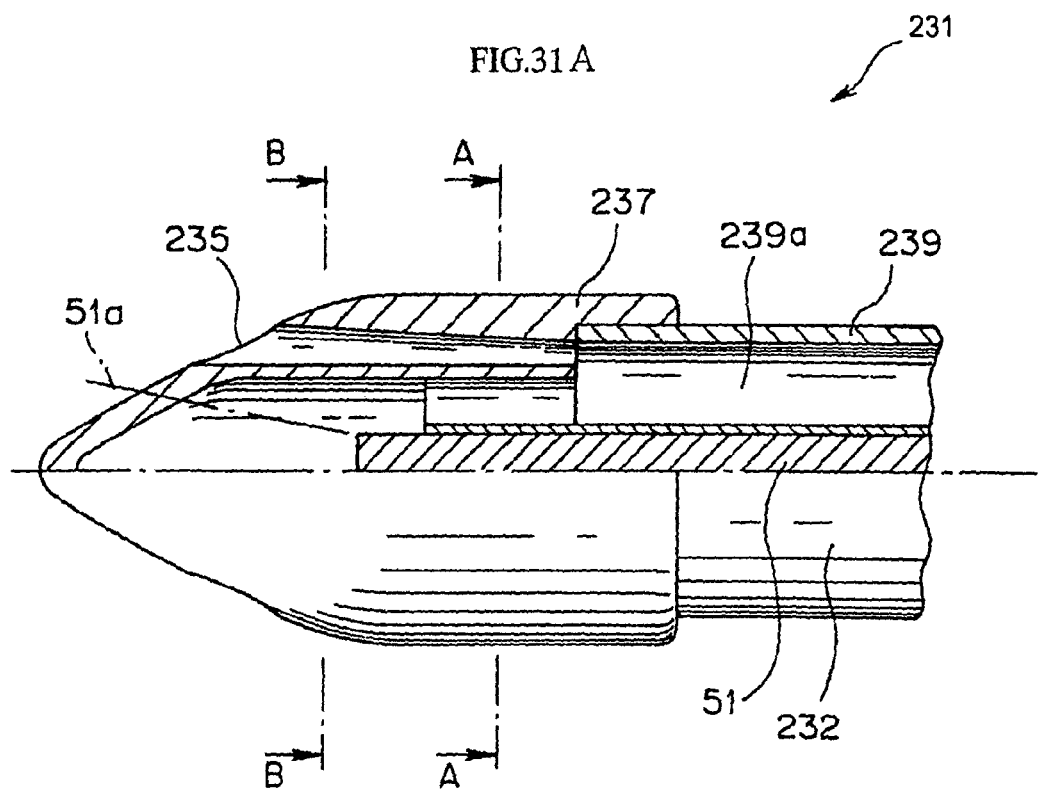
Figure 31B:
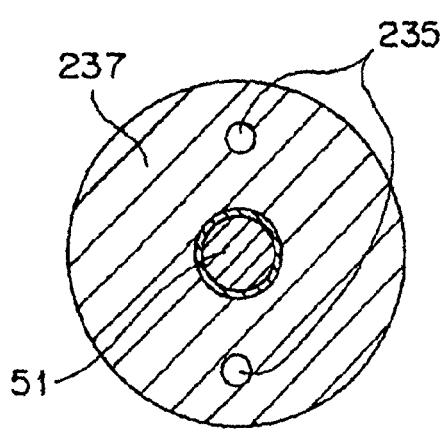
Figure 31C:
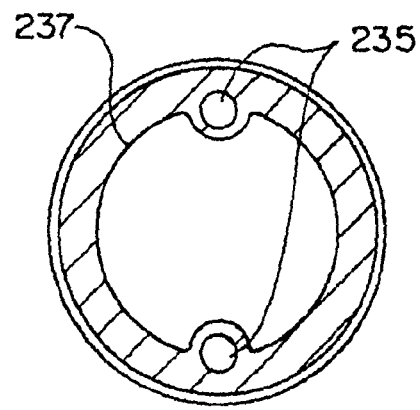

FIGS. 31A, 31B, and 31C are diagrams according to a second modification. FIG. 31A is a cross-sectional view showing the front end portion of a dissector 231. FIG. 31B is a cross-sectional view along an A-A line in FIG. 31A. FIG. 31C is a cross-sectional view along a B-B line in FIG. 31A.

According to the second modification, a dissecting member 237 is fixed to a sheath 239. The dissecting member 237 has a plurality of air holes 235 and the gas introduced to a sealed space 239a is discharged to the outside of an inserting portion 232 via air holes 235. In this case, since the dissecting member 237 is sealed, it is possible to prevent the invasion of fat or body fluid in the field of view 51a of the rigid endoscope 51.

(5) Harvester

Figure 14:
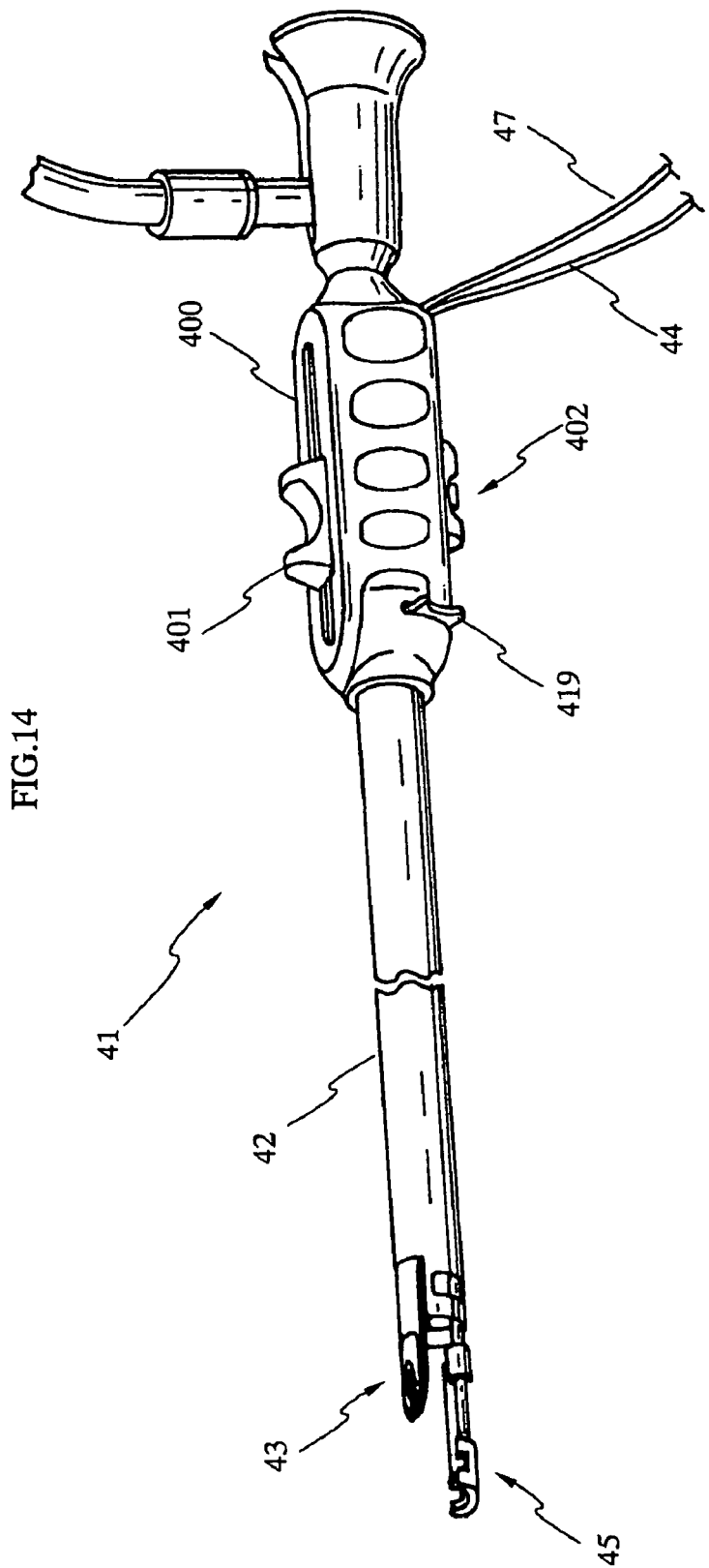
FIG. 14 is a side view showing a harvester.

FIG. 14 is a side view showing the harvester 41. At the front end of the metallic inserting portion 42 of the harvester 41 serving as the living-body tissue removing apparatus, the bipolar cutter 43 is arranged to the top thereof and the vein keeper 45 is arranged to the bottom and inner side thereof. A bipolar cut lever 401 and a vein keeper lever 402 are arranged to the grip portion 400 connected to the base end of the inserting portion 42. The bipolar cut lever 401 and the vein keeper lever 402 advance or return along the longitudinal axis and then the bipolar cutter 43 and the vein keeper 45 advance or return in front of the inserting portion 42 in association with the advance/return operation thereof.

The structure of the harvester 41 on the base end side is the same as that of the dissector 31 on the base end side and therefore a description thereof is omitted (refer to FIG. 13).

Figure 15:
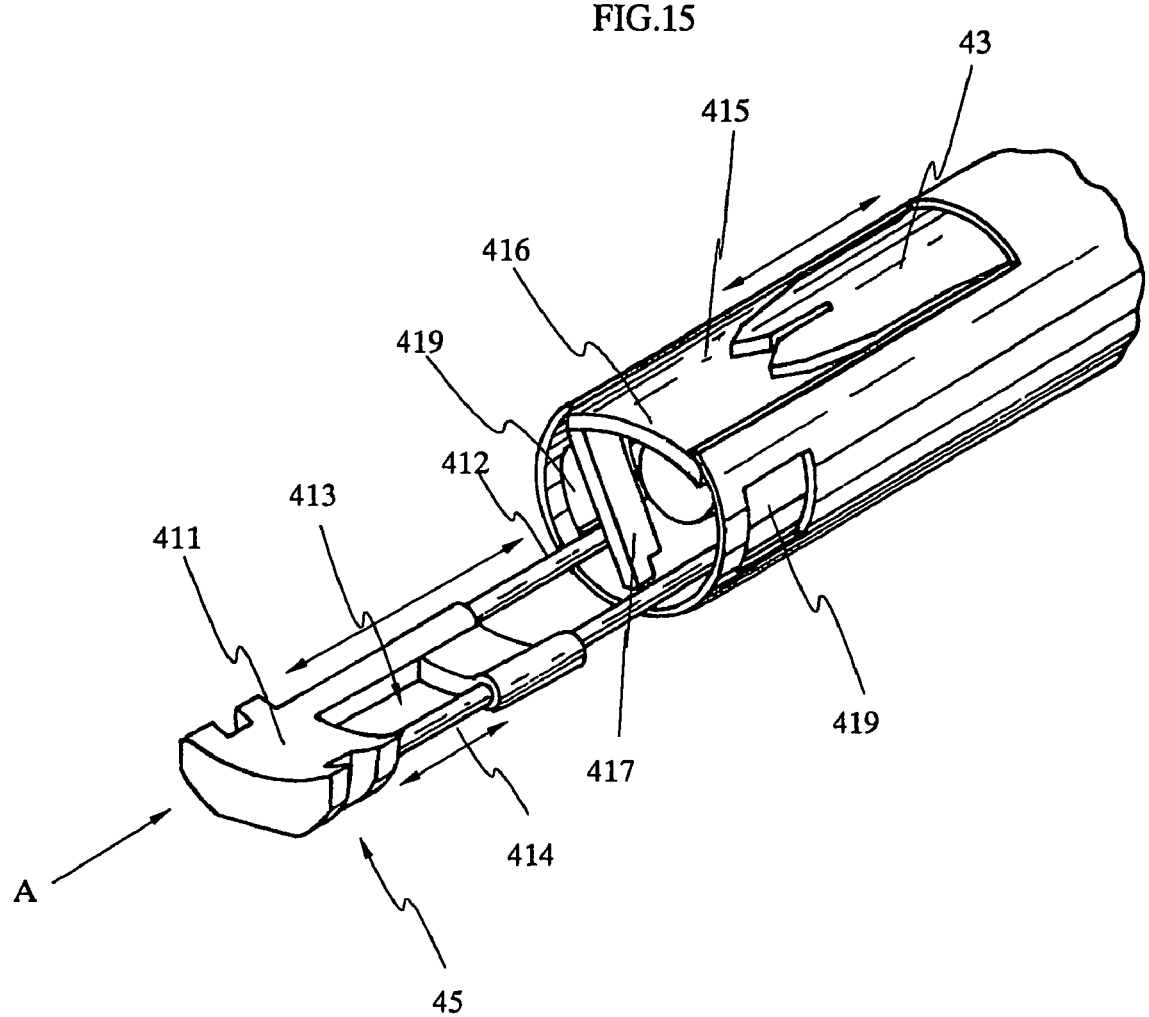
FIG. 15 is a partial perspective view showing the structure of a front end of the harvester.
Figure 16:
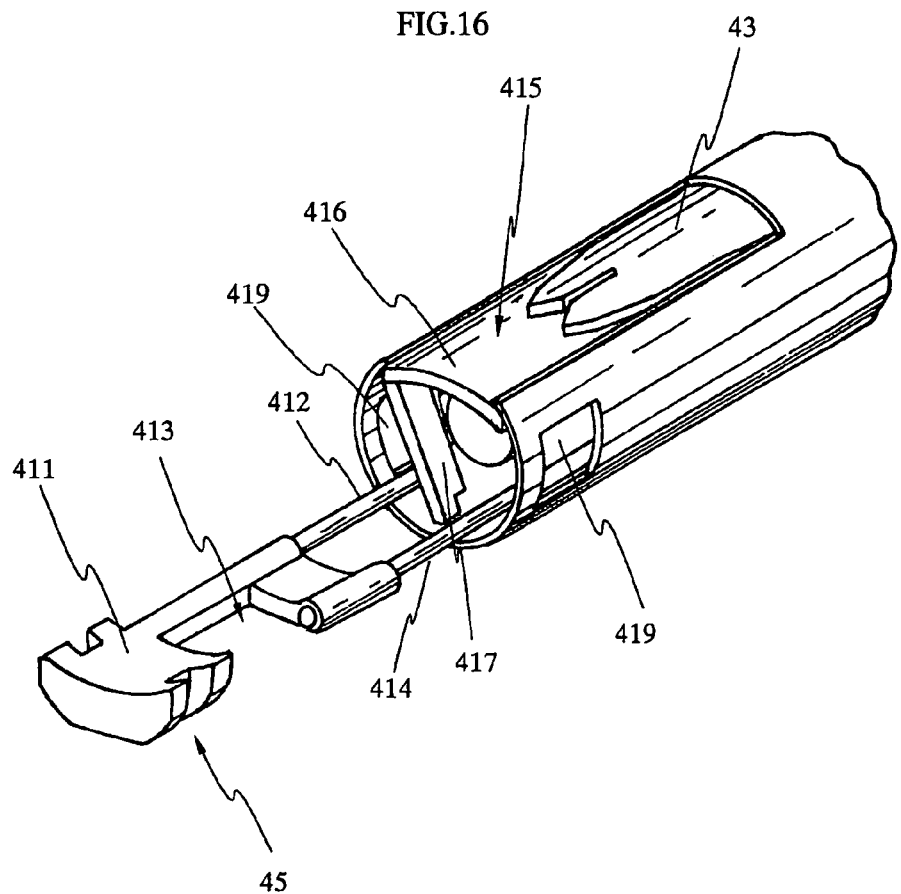
FIG. 16 is a diagram for explaining the operation of a locking shaft shown in FIG. 15.
Figure 17:
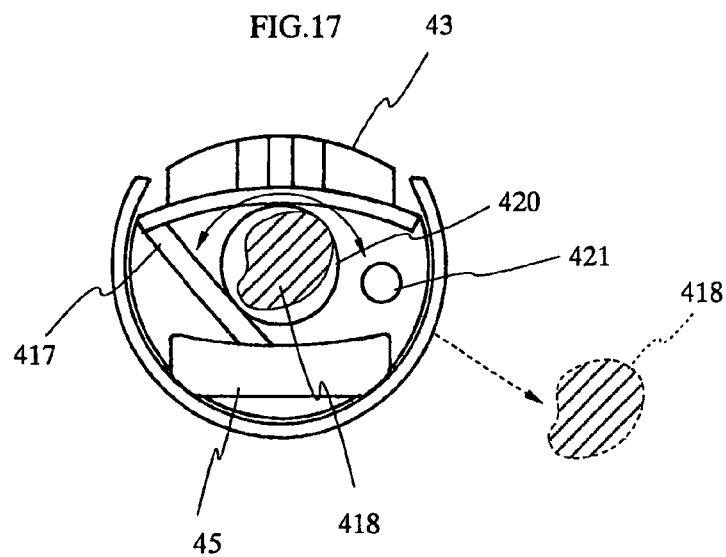
FIG. 17 is a diagram shown in a direction of an arrow A in FIG. 15.

FIG. 15 is a partial perspective view showing the structure of the front end of the harvester 41. FIG. 16 is a diagram for explaining the operation of a locking axis 414 shown in FIG. 15. FIG. 17 is a diagram in a direction of an arrow A in FIG. 15.

Referring to FIG. 15, the vein keeper 45 serving as a blood vessel holding member of the harvester 41 comprises: a blood vessel keeping bed 411 which is U-shaped; a vein keeper shaft 412 which keeps the blood vessel keeping bed 411 that can advance and return in the longitudinal direction; and a locking shaft 414 which advances and returns in the longitudinal axis direction of the blood vessel keeping bed 411, forming a closed space 413 for accommodating the blood vessel in parallel with the vein keeper shaft 412 in the U-shaped blood vessel keeping bed 411. The locking shaft 414 is locked to the blood vessel keeping bed 411 similarly to the vein keeper shaft 412 in the state shown in FIG. 15, thereby forming the space 413. However, the locking state of the locking shaft 414 is reset, thereby releasing the closed space 413 and advancing and returning the blood vessel 11 in the closed space 413 to be accommodated, as shown in FIG. 16.

The front-end side surface of the inserting portion 42 having the bipolar cutter 43 has a notch portion 415. A cutter shaft (which will be described later) for advancing/returning the bipolar cutter 43 is inserted in the inserting portion 42 via the notch portion 415. A guarding portion 416 having the arcuate cross-section is arranged to the inner wall surface of the notch 415. On the front-end inner surface of the inserting portion 42, a wiper 417 for wiping the deposit attached to a window portion of the front end portion of the rigid endoscope 51 is arranged.

That is, in the wiper 417 serving as a wiper member, one end of the wiper 417 functions as a shaft and the other end of the wiper 417 is slid on the surface of the window portion, so as to sweep the deposit adhered to the window portion of the rigid endoscope 51. The one end of the wiper 417 functions as a shaft and then another end of the wiper 417 sweeps an inner side of a guarding portion 416, thereby forming a wiper guarding portion. A part of the cylindrical wiper guarding portion has a sweeping hole 419 serving as a hole portion for externally sweeping a deposit 418 (refer to FIG. 17) wiped by the wiper 417. The deposit 418 includes the blood, fat, and smoke generated by the electric knife.

Referring to FIG. 15, the wiper 417 is arranged to the base end side rather than the front end surface of the tube-shaped inserting portion 42, namely, at the position inside of the inserting portion 42. In order to prevent the removed deposit from being placed in the inserting portion 42 upon sliding the wiper 417 and to sweep the deposit out of the inserting portion 42, the sweeping hole 419 is arranged at the position in the sliding direction of the wiper 417.

Figure 23:
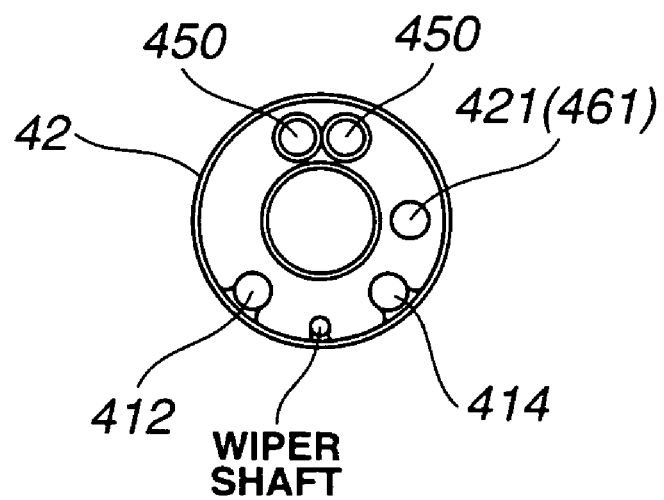
FIG. 23 is a cross-sectional view along an A-A line shown in FIG. 22.

The wiper 417 is swept by a wiper lever 419 (refer to FIG. 14) via a wiper shaft (not shown, refer to FIG. 23). That is, the wiper 417 is rotated at one end of the wiper 417 as the axis on the surface perpendicular to the shaft of the inserting portion 42 by rotating the wiper lever 419 serving as a wiper operating member around the shaft of the grip portion 400.

Referring to FIG. 17 as a diagram in a direction of an arrow A in FIG. 15, an opening of an air feed channel 421 for feeding air and an opening of a rigid-endoscope inserting channel 420, namely, an endoscope opening are adjacently arranged at a predetermined inside portion from the front end surface of the inserting portion 42. The rigid endoscope 51 is inserted through the opening of the rigid-endoscope inserting channel 420.

Figure 18:
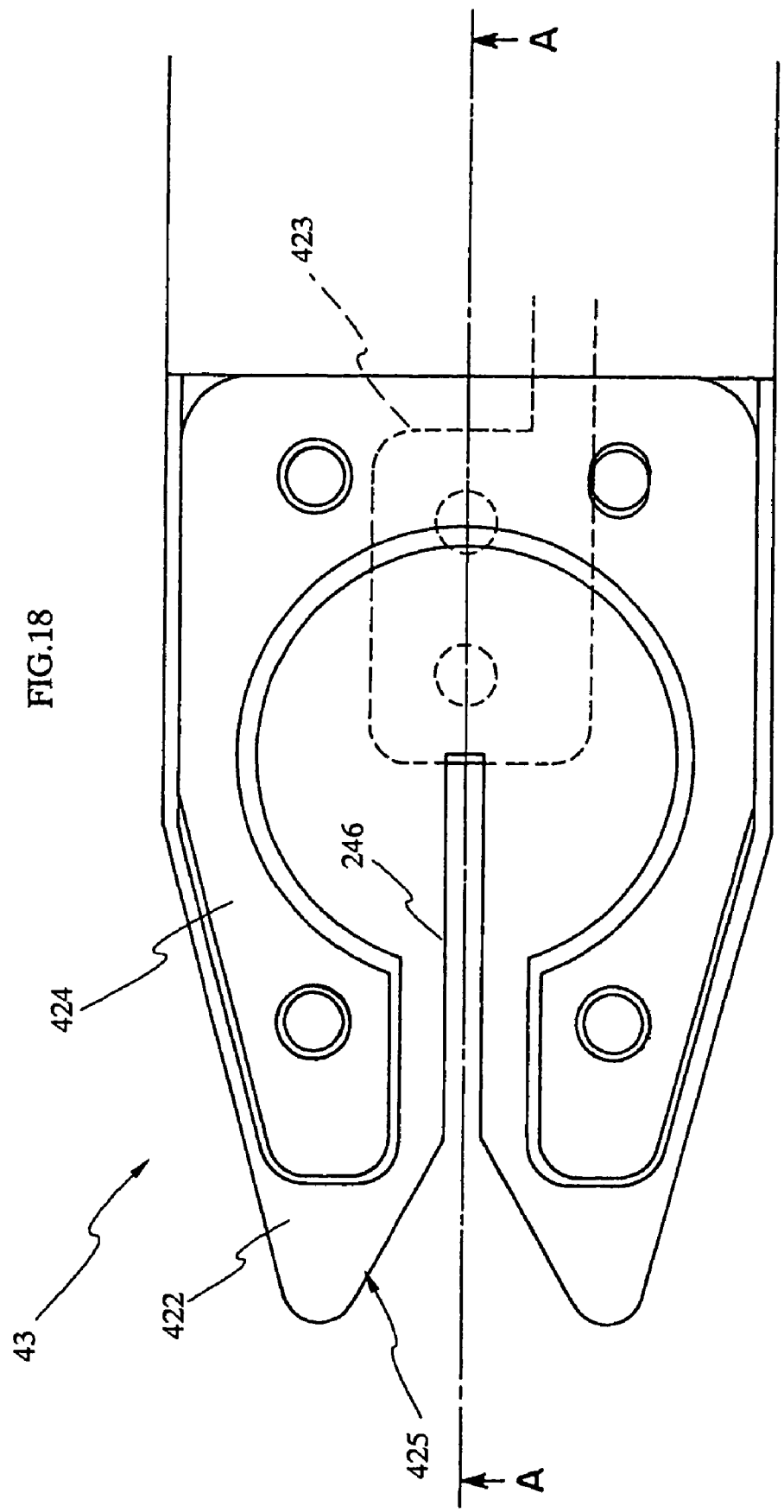
FIG. 18 is a top view showing a bipolar cutter.
Figure 19:
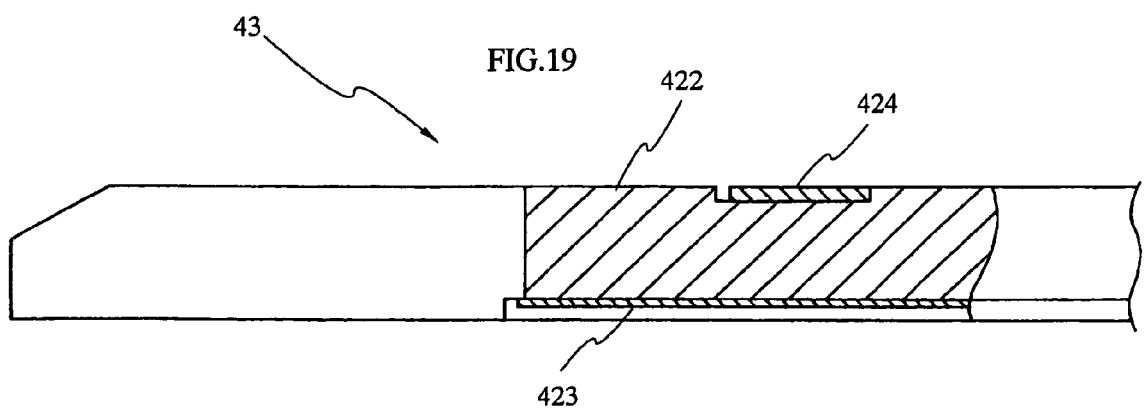
FIG. 19 is a cross-sectional view along an A-A line in FIG. 18.

FIG. 18 is a top view showing the bipolar cutter 43. FIG. 19 is a cross-sectional view showing an A-A cross-section in FIG. 18.

Referring to FIG. 18, the bipolar cutter 43 comprises: a branch keeping member 422 containing a transparent insulating member; an applying electrode 423 as one electrode of the bipolar; and a feedback electrode 424 as another electrode of the bipolar. Referring to FIG. 19, the bipolar cutter 43 comprises the layer structure formed in three-layers construction including the feedback electrode 424, the branch keeping member 422, and the applying electrode 423, arranging the feedback electrode 424 on the top layer.

A V-shaped groove 425 is formed on the front end side of the branch keeping member 422. A slit groove 426 having the width of 0.5 mm is formed on the base end of the V-shaped groove 425.

Upon cutting the branch 11a, the branch 11a is guided to the slit groove 426 along the V-shaped groove 425 of the branch keeping member 422. The branch 11a enters the slit groove 426 to be pressed, thereby keeping the compressing state of the branch 11a into the slit groove 426. In this state, the high-frequency current flows to the feedback electrode 424 from the applying electrode 423, thereby cutting and bleeding-stopping of the branch 11a.

Figure 20:
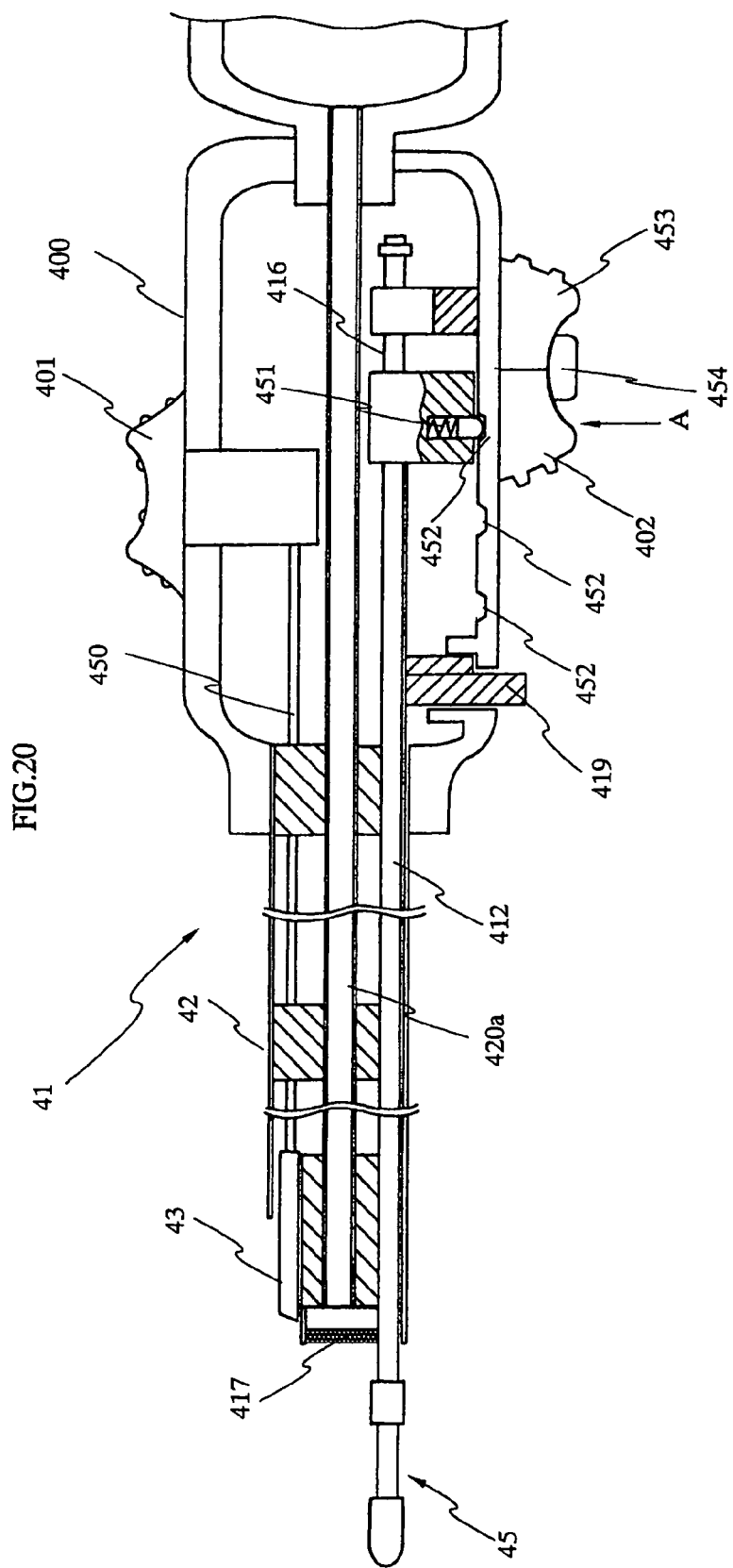
FIG. 20 is a cross-sectional view showing the operation structure of the harvester in the longitudinal axis direction.
Figure 21:
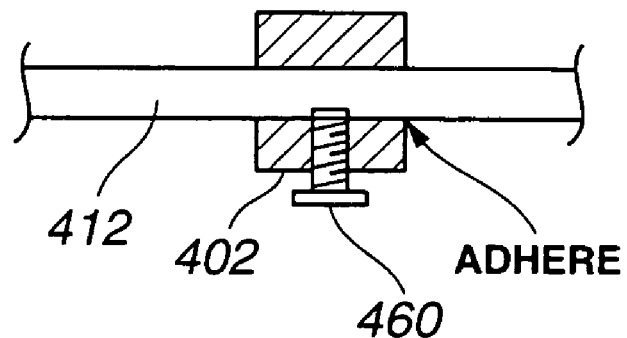
FIG. 21 is a conceptual diagram showing the attachment of a vein keeper 402 from an arrow A shown in FIG. 20.

FIG. 20 is a cross-sectional view showing the operation structure of the harvester 41 in the longitudinal axis direction. FIG. 21 is a conceptual diagram for attachment of the vein keeper lever 402 in the direction of an arrow A shown in FIG. 20.

Referring to FIG. 20, a metallic tube member 420a forming a rigid-endoscope inserting channel 420 is inserted in the harvester 41 along the axial direction of the harvester 41 from the base end side of the grip portion 400 to the front end portion of the inserting portion 42. The rigid-endoscope inserting channel 420 has an endoscope inserting portion for inserting the rigid endoscope 51 at the inserting portion of the harvester 41. The bipolar cutter 43 is connected to the bipolar cut lever 401 arranged to the grip portion 400 by a bipolar shaft 450 inserted in the inserting portion 42. The bipolar cut lever 401 advances and returns along the longitudinal axis. Then, the advancing and returning force is transmitted to the bipolar cutter 43 via the bipolar shaft 450, and the bipolar cutter 43 advances and returns in front of the inserting portion 42.

Similarly, the vein keeper 45 is connected to the vein keeper lever 402 arranged to the grip portion 400 by the vein keeper shaft 412 inserted in the inserting portion 42. The vein keeper lever 402 advances and returns along the longitudinal direction and then the advancing and returning force is transmitted to the vein keeper 45 via the vein keeper shaft 412. Thus, the vein keeper 45 advances and returns in front of the inserting portion 42.

The vein keeper lever 402 and the vein keeper shaft 412 are integrally moved onto the inner surface of the grip portion 400 by a clicking mechanism 451 for pin-pressing the inner surface of the grip portion 400. When the clicking mechanism 451 is at any of three clicking grooves 452 arranged on the inner surface of the grip portion 400, the vein keeper lever 402 and the vein keeper shaft 412 are stably kept. The force acts in the longitudinal axis direction, thereby easily escaping the clicking mechanism 451 from the clicking grooves 452.

The vein keeper lever 402 is detachably connected to a locking lever 453. A locking button 454 is pressed down, thereby separating the vein keeper lever 402 from the locking lever 453. The locking lever 453 is connected to the locking shaft 414, the locking lever 453 advances and returns in the separating state from the vein keeper lever 402, and thus the blood vessel 11 advances and returns to be accommodated in the closed space 413 (refer to FIGS. 15 and 16).

Referring to FIG. 21, the vein keeper lever 402 is fixed to the vein keeper shaft 412 by the adhesion and a screw 460.

Figure 22:
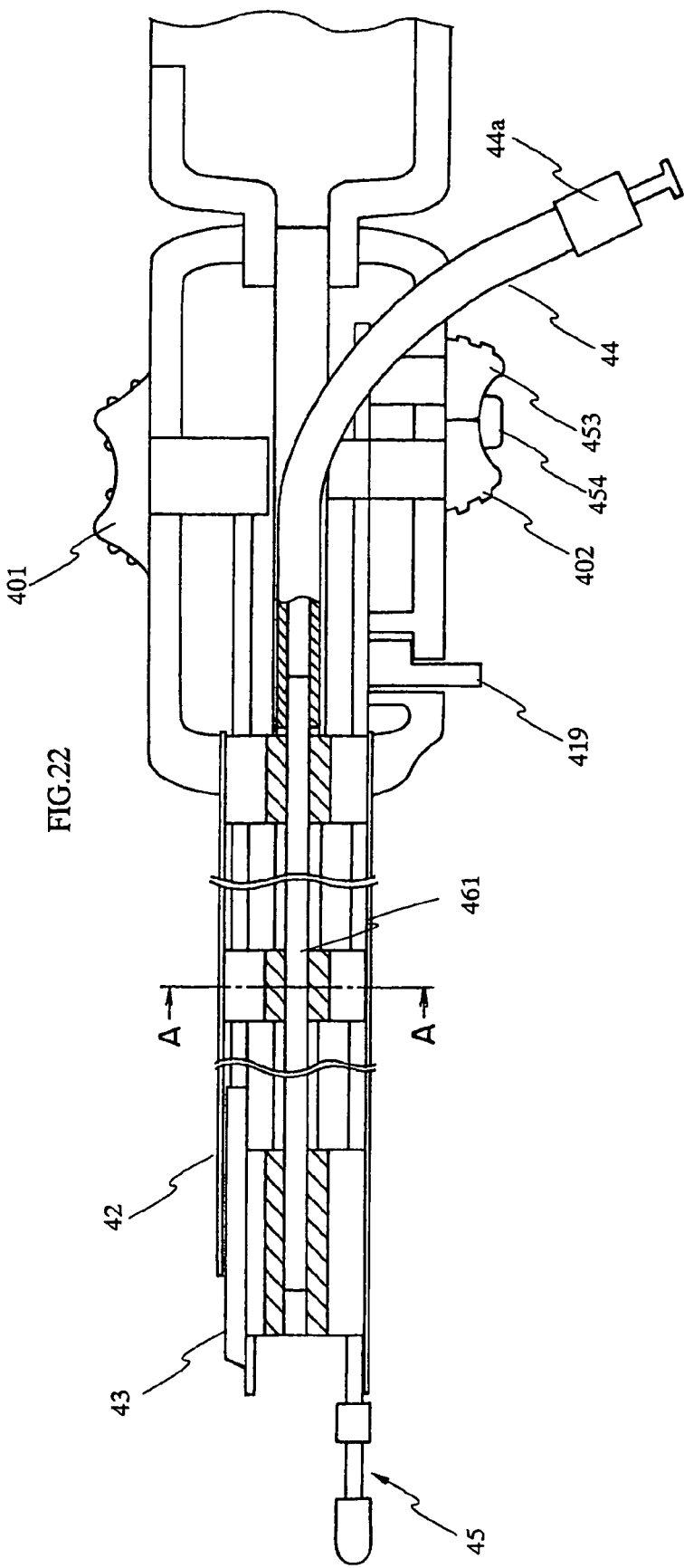
FIG. 22 is a cross-sectional view showing the air feed structure of the harvester in the longitudinal axis direction.

FIG. 22 is a cross-sectional view showing the air feed structure of the harvester 41 in the longitudinal axis direction. FIG. 23 is a cross-sectional view showing the cross section along an A-A line shown in FIG. 22.

Referring to FIG. 22, a metallic air-feed pipe 461 forming an air feed channel 421 is inserted in the harvester 41 along the axial direction of the harvester 41 from the base end side of the grip portion 400 to the front end portion of the inserting portion 42. The air feed tube 44 is fit into the grip portion 400 at one end of the air-feed pipe 461 on the base end side of the grip portion 400. The air feed connector 44a is arranged to the base end of the air feed tube 44. The air feed connector 44a is connected to a connector of a tube connected to the air feed device 108. An air feed pipe 461 has an air feed portion for feeding air of carbon dioxide gas to the inside of the inserting portion of the harvester 41, and further has a discharge port to the outside of the inserting portion 42 from the opening of the front end surface of the inserting portion 42.

Figure 24:
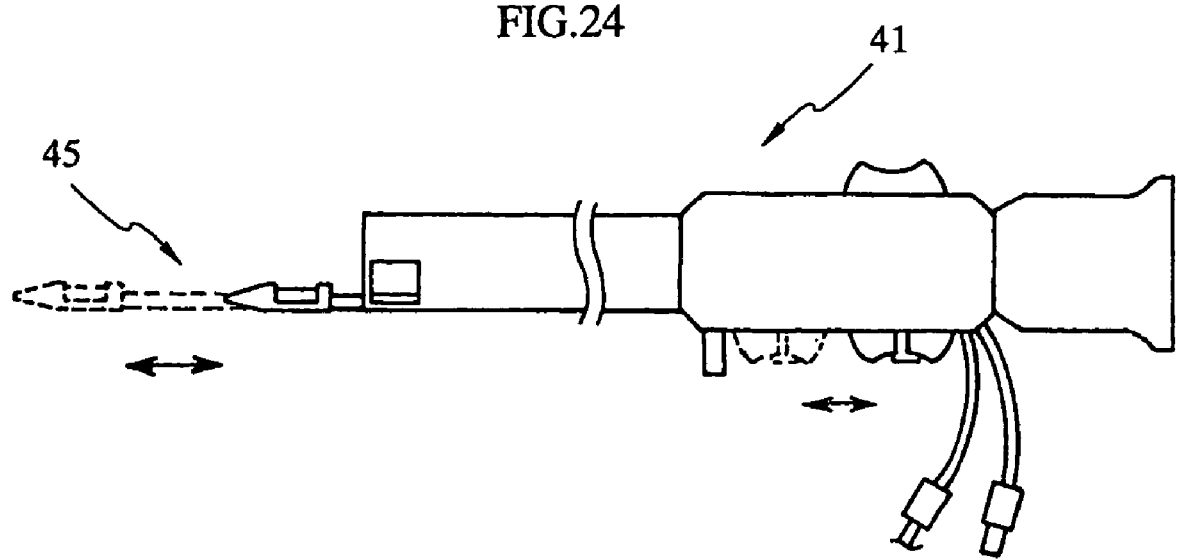
FIG. 24 is a first diagram for explaining the operation of the vein keeper of the harvester.
Figure 25:
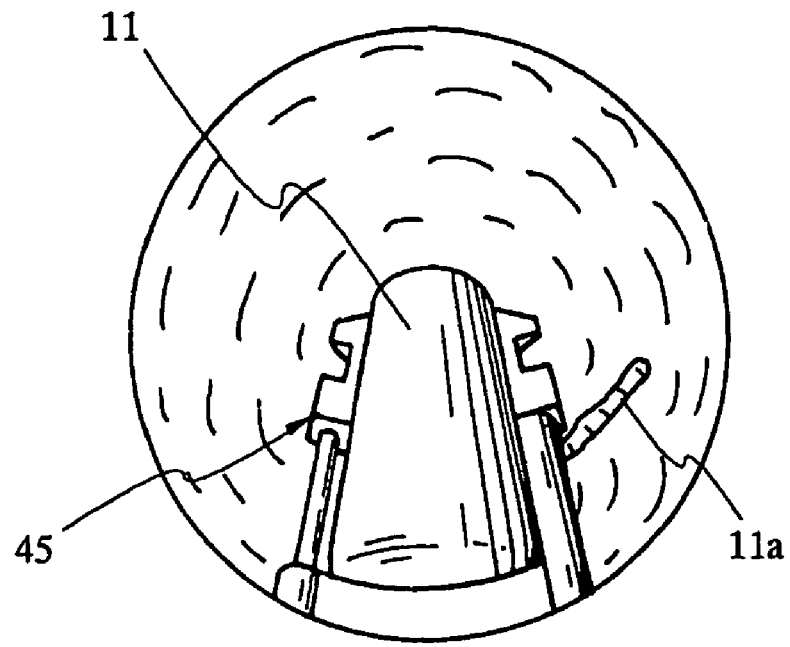
FIG. 25 is a second diagram for explaining the operation of the vein keeper of the harvester.
Figure 26:
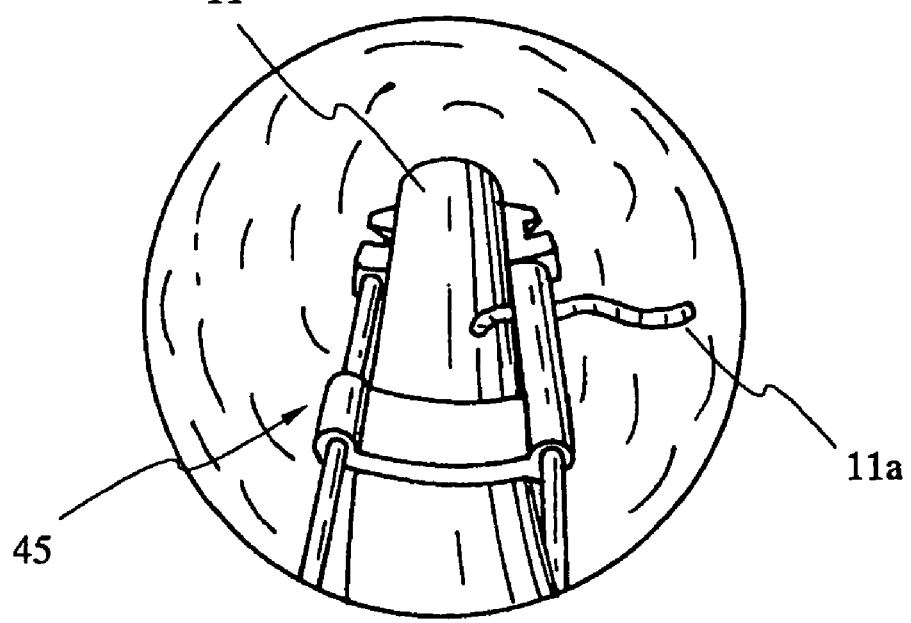
FIG. 26 is a third diagram for explaining the operation of the vein keeper of the harvester.

According to the embodiment, as mentioned above, referring to FIG. 24, the vein keeper lever 402 advances and returns, thereby advancing and returning the vein keeper 45 at the front end. When the endoscope image upon cutting the blood vessel 11 is as shown in FIG. 25 and the state of the branch 11a is not confirmed, referring to FIG. 26, the vein keeper lever 402 advances in the longitudinal axis direction, thereby advancing the vein keeper 45 from the front end. Referring to FIG. 26, it is possible to visually recognize the endoscope image suitable to the confirmation of the state of the branch 11a.

According to the embodiment, referring to FIGS. 27 and 28, the dissector 31 is integrally arranged to the air feed tube 34 and the air feed connector 34a, and the harvester 41 is integrally arranged to the electric cable 47, a connector 470 arranged to the base end of the electric cable 47, the air feed tube 44, and the air feed connector 44a. The dissector 31 and the harvester 41 are disposable.

Figure 29:
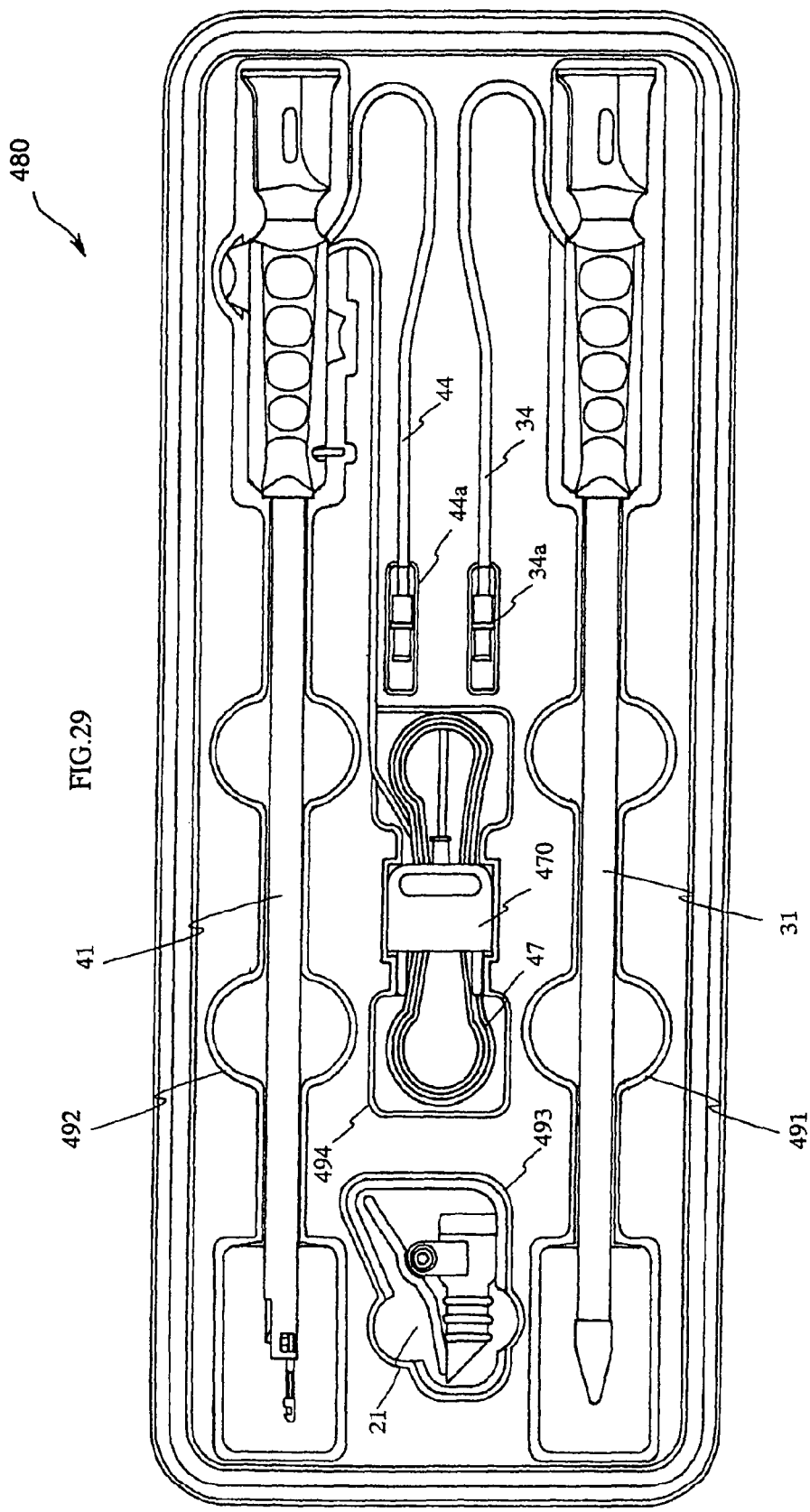
FIG. 29 is a diagram showing an accommodating case which accommodates the dissector and the harvester shown in FIGS. 27 and 28.

The dissector 31 and the harvester 41 are disposable and therefore are accommodated in a disposable accommodating case 480 shown in FIG. 29 together with the trocar 21. The dissector 31 and the harvester 41 are packed in a sterilized pack (not shown) and are conveyed to a desired hospital.

Referring to FIG. 29, the accommodating case 480 comprises: accommodating spaces 491 and 492 for arranging the front end sides of the dissector 31 and the harvester 41 in the same direction; an accommodating space 493 for arranging the trocar 21 provided on the front end side between the dissector 31 and the harvester 41; and an accommodating space 494 for arranging the connector 470 and the electric cable 47 of the harvester 41 placed around the center of the harvester 41 and the dissector 31. Upon accommodating the connector 470 and the electric cable 47 in the accommodating space 494, the connector 470 is used as a cover for preventing the dash-out of the electric cable 47.

What is claimed is:

1. An apparatus for treating a blood vessel in a living-body tissue, the apparatus comprising:
    a grip portion;
    an inserting portion which is connected to the grip portion, wherein the inserting portion has a base end and a front end, and the inserting portion is insertable in the living-body tissue;
    an endoscope channel which is formed along a longitudinal direction of the inserting portion and into which an endoscope is insertable;
    a first channel, a second channel, and a third channel provided along the longitudinal direction of the inserting portion;
    a first support member having a base end and a front end and being movable to advance and return along the first channel, the front end of the first support member being connected to a blood vessel cutting portion for cutting a branch of a blood vessel to be removed;
    a second support member and a third support member which are movable to advance and return along the second channel and the third channel, respectively, and which are arranged parallel to the longitudinal direction of the inserting portion on an opposite side of the endoscope from the first support member, each of the second and third support members having a base end and a front end, and the front ends of the second and third support members being connected to a blood vessel holding member for holding the blood vessel;
    an operating portion which is provided to the grip portion and which is operable to advance and return the blood vessel holding member and the blood vessel cutting portion in the longitudinal direction of the inserting portion; and
    an air feed portion which feeds gas in the inserting portion so as to discharge the gas from an opening arranged in a front end surface of the front end of the inserting portion, the opening being adjacent to an endoscope opening portion of the endoscope channel;
    wherein the gas is fed to and discharged from the opening via the air feed portion;
    wherein the blood vessel holding member comprises a blood vessel keeping bed provided between the second support member and the third support member at the front ends of the second and third support members, the blood vessel keeping bed being movable to travel along the longitudinal direction of the inserting portion while remaining between the second support member and the third support member and while keeping a part of the blood vessel in contact with the blood vessel keeping bed;
    wherein the second support member holds the blood vessel keeping bed such that the blood vessel keeping bed advances and returns along the longitudinal direction of the inserting portion in accordance with movement of the second support member; and
    wherein the third support member is movable to advance and return with respect to the blood vessel keeping bed, such that the third support member is movable to return from the blood vessel keeping bed toward the front end of the inserting portion to open a closed space for accommodating the blood vessel, the closed space being formed by the blood vessel keeping bed, the second support member, and the third support member.

2. The apparatus according to claim 1, wherein the blood vessel cutting portion comprises an electric knife.

3. The apparatus according to claim 1, wherein the blood vessel cutting portion comprises a bipolar cutter.

4. The apparatus of claim 1, wherein the grip portion comprises an actuator for causing a window portion at a front end portion of the endoscope to be cleaned.

5. The apparatus of claim 1, wherein the grip portion comprises an aperture to receive an input responsive to manipulation by an operator, wherein the received input causes deposited material to be removed from a window portion of a front end portion of the endoscope.

6. The apparatus according to claim 1, wherein the blood vessel cutting portion has a planar shape.

7. The apparatus according to claim 1, wherein the blood vessel cutting portion comprises a planar bipolar cutter.

8. The apparatus according to claim 1, wherein the blood vessel holding member holds the blood vessel at a predetermined portion when the second support member and the third support member are simultaneously moved in the longitudinal direction, and the second support member and the third support member connected to the blood vessel keeping bed are stopped to keep the blood vessel parallel to the longitudinal direction.

9. The apparatus according to claim 1, wherein the part of the blood vessel that is kept in contact with the blood vessel keeping bed is a part of the branch of the blood vessel.

10. The apparatus according to claim 1, wherein the blood vessel keeping bed has an arcuate surface and keeps the part of the blood vessel in contact with the arcuate surface.

11. A method for treating a blood vessel in a living-body tissue, the method comprising:
   observing an inside of the living-body tissue by an observing portion provided in an inner space of an inserting portion adapted for insertion into the living-body tissue;
   holding a predetermined blood vessel in the living-body tissue by a blood vessel holding portion;
   cutting a branch of the predetermined blood vessel by a cutting portion, which is movable forward from a front end of the inserting portion, while holding the predetermined blood vessel by the blood vessel holding portion, wherein the blood vessel holding portion has two support members a first support member and a second support member which are movable to advance and return through two channels in the inserting portion, respectively, and wherein the predetermined blood vessel is held by the blood vessel holding portion at a position between the first and second support members while a position of the branch of the predetermined blood vessel is viewed by the observing portion; and
   forming, with a gas, a space at a periphery of the predetermined blood vessel and at a periphery of the branch of the predetermined blood vessel by discharging the gas forward from a front end surface of the inserting portion when cutting the branch of the predetermined blood vessel while holding the predetermined blood vessel;
   wherein the cutting of the branch of the predetermined blood vessel while holding the predetermined blood vessel is performed with the blood vessel holding portion and the cutting portion arranged on opposite sides of a longitudinal central axis of the observing portion;
   wherein the blood vessel holding portion and the cutting portion advance and return substantially in parallel to a longitudinal direction of the observing portion;
   wherein the holding of the blood vessel by the blood vessel holding portion is performed with a blood vessel keeping bed, which is provided between the first and second support members at front ends of the first and second support members, the blood vessel keeping bed being movable along a longitudinal direction of the inserting portion while remaining between the first and second support members and while keeping a part of the blood vessel in contact with the blood vessel keeping bed;
   wherein the first support member holds the blood vessel keeping bed such that the blood vessel keeping bed advances and returns along the longitudinal direction of the inserting portion in accordance with movement of the first support member; and
   wherein the second support member is movable to advance and return with respect to the blood vessel keeping bed, such that the second support member is movable to return from the blood vessel keeping bed toward the front end of the inserting portion to open a closed space for accommodating the blood vessel, the closed space being formed by the blood vessel keeping bed, the first support member, and the second support member.

\* \* \* \* \*